(12) United States Patent
Goh et al.

(10) Patent No.: US 11,827,871 B2
(45) Date of Patent: Nov. 28, 2023

(54) SMALL VOLUME BIOREACTORS WITH SUBSTANTIALLY CONSTANT WORKING VOLUMES AND ASSOCIATED SYSTEMS AND METHODS

(71) Applicants: Massachusetts Institute of Technology, Cambridge, MA (US); Sanofi, Paris (FR)

(72) Inventors: Shireen Goh, Singapore (SG); Rajeev Jagga Ram, Arlington, MA (US); Michelangelo Canzoneri, Dusseldorf (DE); Horst Blum, Kriftel (DE)

(73) Assignees: Massachusetts Institute of Technology, Cambridge, MA (US); Sanofi, Paris (FR)

( * ) Notice: Subject to any disclaimer, the term of this patent is extended or adjusted under 35 U.S.C. 154(b) by 170 days.

(21) Appl. No.: 16/673,805

(22) Filed: Nov. 4, 2019

(65) Prior Publication Data
US 2020/0063082 A1 Feb. 27, 2020

Related U.S. Application Data

(63) Continuation of application No. 14/913,734, filed as application No. PCT/US2014/052252 on Aug. 22, 2014, now Pat. No. 10,479,973.

(60) Provisional application No. 61/869,116, filed on Aug. 23, 2013.

(30) Foreign Application Priority Data

Jul. 17, 2014 (EP) .................................... 14306161

(51) Int. Cl.
  *C12M 3/06* (2006.01)
  *C12M 1/00* (2006.01)
  *C12M 1/34* (2006.01)

(52) U.S. Cl.
  CPC ............ *C12M 23/16* (2013.01); *C12M 23/58* (2013.01); *C12M 41/32* (2013.01); *C12M 41/34* (2013.01); *C12M 41/44* (2013.01)

(58) Field of Classification Search
  CPC ...... C12M 23/16; C12M 23/58; C12M 41/32; C12M 41/44; C12M 41/46
  See application file for complete search history.

(56) References Cited

U.S. PATENT DOCUMENTS

| | | |
|---|---|---|
| 3,658,478 A | 4/1972 | Spergel |
| 4,442,206 A | 4/1984 | Michaels et al. |
| 4,839,292 A | 6/1989 | Cremonese |
| 5,081,035 A | 1/1992 | Halberstadt et al. |
| 5,100,781 A | 3/1992 | Greenbaum |
| 5,188,962 A | 2/1993 | Hasegawa et al. |
| 5,459,069 A | 10/1995 | Palsson et al. |
| 5,856,179 A | 1/1999 | Chen et al. |
| 6,576,458 B1 | 6/2003 | Farzin et al. |
| 7,507,579 B2 | 3/2009 | Boccazzi et al. |
| 10,472,602 B2 | 11/2019 | Goh et al. |
| 10,479,973 B2 | 11/2019 | Goh et al. |
| 11,459,538 B2 | 10/2022 | Goh et al. |
| 2003/0113905 A1 | 6/2003 | Ho et al. |
| 2004/0077075 A1 | 4/2004 | Jensen et al. |
| 2004/0209354 A1 | 10/2004 | Mathies et al. |
| 2005/0026134 A1 | 2/2005 | Miller et al. |
| 2005/0032199 A1 | 2/2005 | Takahashi |
| 2005/0089993 A1 | 4/2005 | Boccazzi et al. |
| 2005/0106045 A1 | 5/2005 | Lee |
| 2005/0164376 A1 | 7/2005 | Balagadde et al. |
| 2006/0019391 A1 | 1/2006 | Marx et al. |
| 2006/0073584 A1 | 4/2006 | Sasaki et al. |
| 2006/0199260 A1 | 9/2006 | Zhang |
| 2006/0281156 A1 | 12/2006 | Aoyama |
| 2007/0036690 A1 | 2/2007 | Miller et al. |
| 2007/0122906 A1 | 5/2007 | Mishra |
| 2007/0148726 A1 | 6/2007 | Auton |
| 2007/0178023 A1 | 8/2007 | Russo et al. |
| 2008/0299539 A1 | 12/2008 | Lee et al. |
| 2010/0035342 A1 | 2/2010 | Cheng et al. |
| 2010/0261242 A1 | 2/2010 | Cheng et al. |
| 2010/0184147 A1 | 7/2010 | Cheng et al. |
| 2011/0207209 A1 | 8/2011 | Hammons et al. |
| 2013/0084622 A1 | 4/2013 | Ram et al. |
| 2014/0120609 A1 | 5/2014 | Goh et al. |
| 2015/0132845 A1 | 5/2015 | Ram et al. |
| 2016/0215246 A1 | 7/2016 | Goh et al. |
| 2017/0107473 A1 | 4/2017 | Goh et al. |
| 2020/0040298 A1 | 2/2020 | Goh et al. |

(Continued)

FOREIGN PATENT DOCUMENTS

| | | |
|---|---|---|
| CN | 1330141 | 1/2002 |
| CN | 2510499 | 9/2002 |
| CN | 1414876 | 4/2003 |

(Continued)

OTHER PUBLICATIONS

Leroux et al., Mar. 2006 Conference: Pittcon 2006 At: Orlando, Florida, USA Ordinal: 450-10 Affiliation: BioProcessors Project: Optical Biosensors for Bioprocessing, 2 pages of PDF.*
Stokelman et al., High Throughput Cell Culture Experimentation with BioProcessors SimCell™ Platform, AMGEN Poster, 2006, 2 pages of PDF.*
Lee et al., Microscale Controlled Continuous Cell Culture, vol. 72, No. 09, 2011.*
Canadian Office Action in Patent Application No. 2888076, dated Jun. 30, 2021, 3 pages.
Canadian Office Action in Patent Application No. 2920083, dated Jun. 22, 2021, 4 pages.

(Continued)

*Primary Examiner* — Kade Ariani
(74) *Attorney, Agent, or Firm* — Fish & Richardson P.C.

(57) ABSTRACT

Control of volume in bioreactors and associated systems is generally described. Feeding and/or sampling strategies can be employed, in some embodiments, such that the working volume within the bioreactor remains substantially constant.

27 Claims, 10 Drawing Sheets

(56) References Cited

U.S. PATENT DOCUMENTS

2022/0411741 A1  12/2022  Goh et al.

FOREIGN PATENT DOCUMENTS

| | | |
|---|---|---|
| CN | 1763173 | 4/2006 |
| CN | 201276562 | 7/2009 |
| CN | 101965394 | 2/2011 |
| CN | 102112595 | 6/2011 |
| CN | 202013342 | 10/2011 |
| CN | 102288653 | 12/2011 |
| EP | 2184354 | 5/2010 |
| JP | 08-089232 | 4/1996 |
| JP | 2000-060596 | 2/2000 |
| JP | 2004-041093 | 2/2004 |
| WO | WO 1990/004425 | 5/1990 |
| WO | WO 2003/093406 | 11/2003 |
| WO | WO 2005/033263 | 4/2005 |
| WO | WO 2007/062218 | 5/2007 |
| WO | WO 2010/017338 | 2/2010 |
| WO | WO 2011/005773 | 1/2011 |
| WO | WO 2011/041508 | 4/2011 |
| WO | WO 2012/107489 | 8/2012 |

OTHER PUBLICATIONS

Indian Office Action in Patent Application No. 201617004633, dated Mar. 22, 2021, 6 pages.
Australian Office Action in Application No. 2014308719, dated Oct. 3, 2019, 10 pages.
Australian Office Action in Application No. 2017279710, dated Feb. 25, 2019, 5 pages.
Australian Office Action in Patent Application No. 2018286560, dated Feb. 10, 2020, 5 pages.
Australian Office Action in Patent Application No. 2013334175, dated Sep. 22, 2016, 8 pages.
Bower et al., "Fed-batch microbioreactor platform for scale down and analysis of a plasmid DNA production process," *Biotechnol. Bioeng.* 109(8):1976-86, Aug. 2012.
Buchenauer et al., "Micro-bioreactors for fed-batch fermentations with integrated online monitoring and microfluidic devices," *Biosensors and Bioelectronics* 29:1411-1416, 2009.
Chinese Office Action in Patent Application No. 201380061624.8, dated Feb. 1, 2016, 11 pages.
Chinese Office Action in Patent Application No. 201480046215.5, dated Dec. 22, 2016, 18 pages.
Chinese Office Action in Patent Application No. 201480046215.5, dated May 2, 2018, 7 pages.
Chinese Office Action in Patent Application No. 201480046215.5, dated Oct. 23, 2017, 18 pages.
Chinese Office Action in Patent Application No. 201380061861.4, dated Jan. 13, 2016, 7 pages.
Chinese Office Action in Patent Application No. 201380061861.4, dated Aug. 1, 2016, 8 pages.
Chinese Office Action in Patent Application No. 201380061861.4, dated Mar. 16, 2017, 4 pages.
Chinese Office Action in Patent Application No. 201380061624.8, dated Feb. 1, 2016.
European Communication in Patent Application No. 13786597.8, dated Sep. 26, 2018, 6 pages.
Examination Report for Singapore Patent Application No. 11201502926T, dated Feb. 2, 2017, 5 pages.
Extended European Search Report in Patent Application No. 14838740.0, dated Mar. 15, 2017, 7 pages.
Goh et al. "Abstract: Microfluidic Scale-Down of Upstream Biopharmaceutical Production," _AIChE Annual Meeting, Oct. 28-Nov. 2, 2012, Pittsburgh, PA.
Goh et al., "Impedance spectroscopy for in situ biomass measurements in microbioreactors, " Proc. 14th International Conference on Miniaturized Systems and Life Sciences, pp. 1556-1558, Oct. 2010.
Heo et al., "Characterization and resolution of evaporation-mediated osmolality shifts that constrain microfluidic cell culture in poly (dimethylsiloxane) devices," *Analytical Chemistry* 79(3):1126-1134, Feb. 2007.
International Preliminary Report on Patentability in International Application No. PCT/US2014/052252, dated Feb. 23, 2016, 6 pages.
International Preliminary Report on Patentability in International Application No. PCT/US2013/066832, dated Apr. 28, 2015, 8 pages.
International Preliminary Report on Patentability in International Application No. PCT/US2013/066845, dated Apr. 28, 2015, 9 pages.
International Search Report and Written Opinion in International Application No. PCT/US2014/52252, dated Nov. 6, 2014, 8 pages.
International Search Report and Written Opinion in International Application No. PCT/US2013/066832, dated Jan. 27, 2014, 10 pages.
International Search Report and Written Opinion in International Application No. PCT/US2013/066845, dated Jun. 3, 2014, 13 pages.
Invitation to Pay Additional Fees dated Mar. 27, 2014, for Application No. PCT/US2013/066845, 5 pages.
Laritz et al., "A microfluidic pH-regulation system based on printed circuit board technology," *Sensors and Actuators* 84:230-235, 2000.
Linek et al., "Measurement of aeration capacity of fermenters," *Chem. Eng. Technol.* 12(1):213-217, 1989.
Mexican Office Action in Patent Application No. MX/a/2015/005284, dated Jan. 21, 2019, 7 pages.
Mexican Office Action in Patent Application No. MX/a/2015/005284, dated Jan. 24, 2020, 6 pages.
Mexican Office Action in Patent Application No. MX/a/2015/005285, dated Feb. 6, 2020, 8 pages.
Mexican Office Action in Patent Application No. MX/a/2016/002331, dated Feb. 11, 2020, 6 pages.
Muller et al., "Fluorescence optical sensor for low concentrations of dissolved carbon dioxide," *Analyst* 121:339-343, Mar. 1996.
Singapore Examination Report in Patent Application No. 11201601068Y, dated Nov. 20, 2017, 4 pages.
Singapore Search Report and Written Opinion in Patent Application No. 11201601068Y, dated May 26, 2017, 15 pages.
Singapore Written Opinion in Patent Application No. 11201502917T, dated Feb. 23, 2018, 4 pages.
Singapore Written Opinion in Patent Application No. 11201502917T, dated Jul. 25, 2017, 4 pages.
Singapore Written Opinion in Patent Application No. 11201502917T, dated Oct. 25, 2013, 5 pages.
Szita et al., "Development of a multiplexed microbioreactor system for high-throughput bioprocessing," *Lab Chip* 5(8):819-26, Aug. 2005.
Thomas et al., "15th International Conference on Miniaturized Systems for Chemistry and Life Sciences," Oct. 2-6, 2011, Seattle, WA USA, pp. 1520-1522.
Wu et al., "Microfluidic cell culture systems for drug research," *Lab Chip* 10:939-956, Jan. 2010.
Australian Office Action in Patent Application No. 2019283934, dated Feb. 12, 2021, 5 pages.
Canadian Office Action in Patent Application No. 2887987, dated Jul. 9, 2021, 1 page.
Chinese Office Action in Patent Application No. 201710541756.0, dated Dec. 3, 2020, 4 pages.
Final Office Action in U.S. Appl. No. 15/161,112, dated Dec. 2, 2020, 20 pages.
Australian Office Action in Patent Application No. 2013334168, dated Nov. 24, 2017, 4 pages.
Australian Office Action in Patent Application No. 2013334168, dated Sep. 24, 2018, 3 pages.
Australian Office Action in Patent Application No. 2013334175, dated Sep. 14, 2017, 3 pages.
Australian Office Action in Patent Application No. 2014308719, dated Dec. 9, 2019, 3 pages.
Australian Office Action in Patent Application No. 2014308719, dated Jan. 30, 2019, 5 pages.

(56) References Cited

OTHER PUBLICATIONS

Australian Office Action in Patent Application No. 2017279710, dated Sep. 4, 2019, 3 pages.
Canadian Office Action in Patent Application No. 2,887,987, dated Jul. 29, 2019, 4 pages.
Canadian Office Action in Patent Application No. 2,887,987, dated Jun. 30, 2020, 3 pages.
Canadian Office Action in Patent Application No. 2,888,076, dated Jul. 26, 2019, 3 pages.
Canadian Office Action in Patent Application No. 2,888,076, dated Jun. 19, 2020, 3 pages.
Canadian Office Action in Patent Application No. 2,920,083, dated Jun. 9, 2020, 4 pages.
Chinese Office Action in Patent Application No. 201380061861.4, dated Jul. 13, 2017, 4 pages.
Chinese Office Action in Patent Application No. 201710541756.0, dated Aug. 8, 2019, 15 pages.
European Office Action in Patent Application No. 13786602.6, dated Oct. 1, 2018, 6 pages.
Final Office Action in U.S. Appl. No. 14/064,021, dated Apr. 14, 2016, 8 pages.
Final Office Action in U.S. Appl. No. 14/064,021, dated Aug. 16, 2018, 10 pages.
Final Office Action in U.S. Appl. No. 14/064,021, dated Sep. 1, 2017, 8 pages.
Final Office Action in U.S. Appl. No. 14/913,734, dated Jul. 30, 2018, 9 pages.
Final Office Action in U.S. Appl. No. 14/913,734, dated Oct. 25, 2017, 9 pages.
Final Office Action in U.S. Appl. No. 15/161,112, dated Jul. 29, 2019, 8 pages.
Mexican Office Action in Patent Application No. MX/a/2015/005284, dated Aug. 14, 2020, 3 pages.
Mexican Office Action in Patent Application No. MX/a/2015/005284, dated Aug. 7, 2019, 9 pages.
Mexican Office Action in Patent Application No. MX/a/2015/005285, dated Aug. 7, 2019, 8 pages.
Non-Final Office Action in U.S. Appl. No. 14/064,021, dated Feb. 28, 2017, 9 pages.
Non-Final Office Action in U.S. Appl. No. 14/064,021, dated Mar. 8, 2018, 8 pages.
Non-Final Office Action in U.S. Appl. No. 14/064,021, dated Sep. 24, 2015, 7 pages.
Non-Final Office Action in U.S. Appl. No. 14/913,734, dated Feb. 23, 2018, 9 pages.
Non-Final Office Action in U.S. Appl. No. 14/913,734, dated Jan. 30, 2019, 10 pages.
Non-Final Office Action in U.S. Appl. No. 14/913,734, dated May 12, 2017, 9 pages.
Non-Final Office Action in U.S. Appl. No. 15/161,112, dated Dec. 14, 2018, 16 pages.
Non-Final Office Action in U.S. Appl. No. 15/161,112, dated Mar. 6, 2020, 6 pages.
Singapore Office Action in Patent Application No. 10201704655S, dated Nov. 12, 2020, 10 pages.
Singapore Office Action in Patent Application No. 11201502917T, dated Apr. 4, 2016, 8 pages.
Singapore Office Action in Patent Application No. 10201800558W, dated Oct. 11, 2021, 11 pages.
Australian Office Action in Patent Application No. 2020250287, dated Jul. 14, 2021, 2 pages.
Australian Office Action in Patent Application No. 2018286560, dated Jul. 10, 2020, 5 pages.
Chinese Office Action in Patent Application No. 201710541756.0, dated Jun. 22, 2020, 7 pages.
European Office Action in Patent Application No. 14838740.0, dated Oct. 2, 2020, 5 pages.
Indian Office Action in Patent Application No. 3033/DELNP/2015, dated Sep. 1, 2020, 6 pages.
Mexican Office Action in Patent Application No. MX/a/2016/002331, dated Jul. 21, 2020, 10 pages.
Singapore Office Action in Patent Application No. 10201803572U, dated Oct. 11, 2021, 9 pages.
Chinese Office Action in Patent Application No. 201710893727.0, dated Mar. 5, 2021, 12 pages.
European Office Action in Patent Application No. 13786597.8, dated May 4, 2021, 4 pages.
European Office Action in Patent Application No. 13786602.6, dated Apr. 30, 2021, 3 pages.
Non-Final Office Action in U.S. Appl. No. 15/161,112, dated May 13, 2021, 27 pages.
Australian Office Action in Patent Application No. 2020201975, dated Mar. 16, 2021, 7 pages.
Indian Office Action in Patent Application No. 3093/DELNP/2015, dated Feb. 22, 2021, 6 pages.
Singapore Office Action in Patent Application No. 10201704655S, dated Jan. 20, 2021, 4 pages.
Office Action in Australian Patent Application No. 2020201975, dated Jan. 4, 2022, 3 pages.
Office Action in Canadian Patent Application No. 2888076, dated Feb. 23, 2022, 3 pages.
Office Action in Chinese Patent Application No. 201710541756.0, dated Mar. 20, 2020, 5 pages.
Office Action in Chinese Patent Application No. 201710893727.0, dated Mar. 3, 2020, 11 pages.
Non-Final Office Action in U.S. Appl. No. 16/654,808, dated Dec. 29, 2021, 15 pages.
Extended Search Report in European Patent Application No. 22158223.2, dated Jul. 4, 2022, 6 pages.
Office Action in Australian Patent Application No. 2022200770, dated Mar. 29, 2023, 5 pages.

\* cited by examiner

| Valve | Name | NO | NC |
|---|---|---|---|
| 1 | Gas Mix 1 | Gas Mix 2 (3 Psi) | Gas Mix 3 (3 Psi) |
| 2 | Reservoir Input | Valve On (15 Psi) | Valve Off (Atm) |
| 3 | Injection 1 | Valve On (15 Psi) | Valve Off (Atm) |
| 4 | Injection 2 | Valve On (15 Psi) | Valve Off (Atm) |
| 5 | Injection 3 | Valve On (15 Psi) | Valve Off (Atm) |
| 6 | Injection 4 | Valve On (15 Psi) | Valve Off (Atm) |
| 7 | Injection 5 (Water) | Valve On (15 Psi) | Valve Off (Atm) |
| 8 | Pump 1 | Valve On (15 Psi) | Valve Off (Atm) |

(a) Valves 1-8

| Valve | Name | NO | NC |
|---|---|---|---|
| 9 | Gas Mix 2 | Nitrogen (3 Psi) | Oxygen (3 Psi) |
| 10 | Pump 2 | Valve Off (Atm) | Valve On (15 Psi) |
| 11 | Pump 3 | Valve On (15 Psi) | Valve Off (Atm) |
| 12 | Sample Reservoir | Valve On (15 Psi) | Valve Off (Atm) |
| 13 | Sample In | Valve On (15 Psi) | Valve Off (Atm) |
| 14 | Sample Out | Valve On (15 Psi) | Valve Off (Atm) |
| 15 | Sample Air In | Valve On (15 Psi) | Valve Off (Atm) |
| 16 | Gas Mix 3 | Nitrogen (3 Psi) | $CO_2$ (3 Psi) |

(b) Valves 9-16

| Valve | Name | NO | NC |
|---|---|---|---|
| 17 | Mixer Bottom Out | Mixer Off (Atm) | Blocked |
| 18 | Mixer Bottom In | Blocked | Mixer On (3 Psi) |
| 19 | Mixer Left Out | Mixer Off (Atm) | Blocked |
| 20 | Mixer Left In | Blocked | Mixer On (3 Psi) |
| 21 | Mixer Top Out | Mixer Off (Atm) | Blocked |
| 22 | Mixer Top In | Blocked | Mixer On (3 Psi) |
| 23 | Reservoir Pressure | Res. Off (Atm) | Res. On (1.5 Psi) |
| 24 | Gas Mix 4 | Available | Available |

(c) Valves 17-24

*FIG. 8*

SMALL VOLUME BIOREACTORS WITH SUBSTANTIALLY CONSTANT WORKING VOLUMES AND ASSOCIATED SYSTEMS AND METHODS

RELATED APPLICATIONS

This application is a continuation of U.S. patent application Ser. No. 14/913,734, filed on Feb. 23, 2016, which is a national stage filing under 35 U.S.C. § 371 of International Application Number PCT/US2014/052252, filed Aug. 22, 2014, entitled "Small Volume Bioreactors with Substantially Constant Working Volumes and Associated Systems and Methods" which claims priority to U.S. Provisional Patent Application Ser. No. 61/869,116, filed Aug. 23, 2013, and entitled "Small Volume Bioreactors with Substantially Constant Working Volumes and Associated Systems and Methods," each of which is incorporated herein by reference in its entirety for all purposes. International Application Number PCT/US2014/052252 also claims priority to European Patent Application Number EP 14306161.2, filed Jul. 17, 2014, and entitled "Small Volume Bioreactors with Substantially Constant Working Volumes and Associated Systems and Methods," which is incorporated herein by reference in its entirety for all purposes.

TECHNICAL FIELD

Control of volume in small volume bioreactors and associated systems is generally described.

SUMMARY

Small volume bioreactors with substantially constant working volumes, and associated systems and methods, are generally described. In certain embodiments, feeding and/or sampling strategies can be employed such that the working volume within the bioreactor remains substantially constant. The bioreactors may be operated in a fed-batch mode of operation, in some embodiments. The subject matter of the present invention involves, in some cases, interrelated products, alternative solutions to a particular problem, and/or a plurality of different uses of one or more systems and/or articles.

Certain embodiments relate to a method of operating a bioreactor. The method comprises, in some embodiments, performing, within the bioreactor, a biochemical reaction in which at least one eukaryotic cell is grown within a liquid medium having a volume of less than about 50 milliliters; adding a first amount of liquid to the liquid medium in the bioreactor during the biochemical reaction; and removing a second amount of liquid from the liquid medium in the bioreactor during the biochemical reaction. In some such embodiments, during at least about 80% of the time over which the biochemical reaction is performed including during the adding and removing steps, the total volume of liquid within the bioreactor does not fluctuate by more than about 20% from an average of the volume of liquid within the bioreactor.

In certain embodiments, the method comprises performing, within the bioreactor, a biochemical reaction within a liquid medium having a volume of less than about 50 milliliters; adding a first amount of liquid to the liquid medium in the bioreactor during the biochemical reaction; and removing a second amount of liquid from the liquid medium in the bioreactor during the biochemical reaction. In some such embodiments, during at least about 80% of the time over which the biochemical reaction is performed including during the adding and removing steps, the total volume of liquid within the bioreactor does not fluctuate by more than about 20% from an average of the volume of liquid within the bioreactor, and the osmolarity of the liquid medium within the bioreactor is maintained within a range of from about 200 osmoles per kilogram of the liquid medium to about 600 osmoles per kilogram of the liquid medium.

According to some embodiments, the method comprises performing, within the bioreactor, a biochemical reaction in which at least one eukaryotic cell is grown within a liquid medium having a volume of less than about 50 milliliters; adding a first amount of liquid to the liquid medium in the bioreactor during a first period of time over which the biochemical reaction is performed; and removing a second amount of liquid having a volume that is within 10% of a volume of the first amount of liquid from the liquid medium in the bioreactor during a second period of time over which the biochemical reaction is performed that does not overlap with the first period of time; and repeating the adding a removing steps at least one time. In some such embodiments, the adding step and the removing step are performed such that, between the adding step and the removing step, substantially no liquid is removed from the bioreactor via a non-evaporative pathway, and substantially no liquid is added to the bioreactor.

The method comprises, in certain embodiments, performing, within the bioreactor, a biochemical reaction within a liquid medium having a volume of less than about 50 milliliters; adding a first amount of liquid to the liquid medium in the bioreactor during a first period of time over which the biochemical reaction is performed; removing a second amount of liquid having a volume that is within 10% of a volume of the first amount of liquid from the liquid medium in the bioreactor during a second period of time over which the biochemical reaction is performed that does not overlap with the first period of time; and repeating the adding a removing steps at least one time. In some such embodiments, the adding step and the removing step are performed such that, between the adding step and the removing step, substantially no liquid is removed from the bioreactor via a non-evaporative pathway, and substantially no liquid is added to the bioreactor. In some such embodiments, during at least about 80% of the time over which the biochemical reaction is performed, the osmolarity of the liquid medium within the bioreactor is maintained within a range of from about 200 osmoles per kilogram of the liquid medium to about 600 osmoles per kilogram of the liquid medium.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 8 is a table outlining the operation of a plurality of valves in an exemplary bioreactor, according to one set of embodiments;

DETAILED DESCRIPTION

Figure 1:
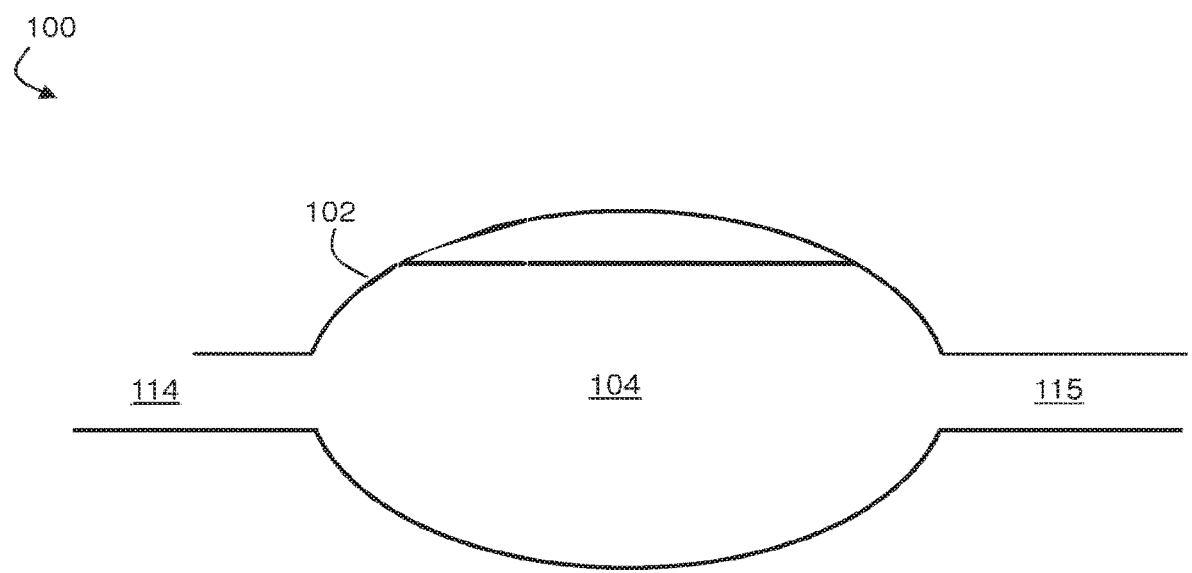
FIG. 1 is an exemplary cross-sectional side view schematic illustration of a bioreactor, according to one set of embodiments.

Control of volume in bioreactors and associated systems is generally described. Feeding and/or sampling strategies can be employed, in some embodiments, such that the working volume within the bioreactor remains substantially constant.

In certain embodiments, the bioreactors described herein are configured to contain a relatively small volume of liquid (e.g., less than 50 milliliters). For many small volume bioreactors, even small changes in volume can lead to large deviations in the process conditions, such as gas transfer rate, mixing rate, and the like. According to certain embodiments, strategies are employed such that the volume of the liquid within the bioreactor is kept constant even after feeding and/or sampling have occurred. For example, in certain instances, the volume of liquid within the bioreactor is maintained such that the volume does not deviate from the average volume by more than 20%. This can be achieved, for example, by adjusting the volume of liquid removed from and/or added to the bioreactor such that the volume of liquid within the bioreactor is maintained within a relatively narrow range of volumes. For example, in certain embodiments, if the volume of the liquid within the bioreactor increases beyond a certain level, the sampling volume is increased so as to keep the volume within the desired range. In some embodiments, if the volume of the liquid within the bioreactor decreases below a certain level, the volume of liquid fed to the bioreactor can be increased to maintain a substantially constant volume of liquid within the bioreactor.

The bioreactors described herein can be configured to perform a variety of suitable biochemical reactions. In some embodiments, the bioreactor can be configured to grow at least one biological cell. The cells within the bioreactor can be suspended in a liquid medium, such as any common cell growth medium known to those of ordinary skill in the art. Certain embodiments involve performing, within the bioreactor, a biochemical reaction in which at least one eukaryotic cell is grown within a liquid medium having a volume of less than about 50 milliliters.

In some embodiments, the osmolarity of the liquid medium within the bioreactor can be maintained within a desirable range. For example, in certain embodiments, the osmolarity of the liquid medium within the bioreactor can be maintained within a range of from about 200 osmoles per kilogram of the liquid medium to about 600 osmoles per kilogram of the liquid medium. Maintaining the osmolarity within this range can be useful for growing eukaryotic cells, which generally require different salinity conditions than prokaryotic cells for proper cell growth.

As noted above, in some embodiments, the volume of the liquid within the bioreactor is maintained within a desirable range. This can be helpful, according to certain embodiments, in controlling conditions within the bioreactor during the biochemical reaction (e.g., during cell growth). Certain embodiments comprise adding a first amount of liquid (e.g., containing at least one biochemical reactant, such as a cell growth medium) to the liquid medium in the bioreactor during the biochemical reaction and removing a second amount of liquid (e.g., containing at least one biochemical reaction product, such as a biological cell) from the liquid medium in the bioreactor during the biochemical reaction. The first amount of liquid can be added over a first period of time over which the biochemical reaction is performed. The second amount of liquid can be removed during second period of time over which the biochemical reaction is performed. In some embodiments, the second period of time does not substantially overlap with the first period of time. The adding and removing steps can be repeated at least one time during operation of the bioreactor.

In some such embodiments, the amounts of liquid added and/or removed can be selected such that during at least about 80% of the time over which the biochemical reaction is performed including during the adding and removing steps, the total volume of liquid within the bioreactor does not fluctuate by more than about 20% from an average of the volume of liquid within the bioreactor. In certain embodiments, the second amount of liquid that is removed from the bioreactor has a volume that is within 10% of the volume of the first amount of liquid that is added to the bioreactor. In some embodiments, the second volume of liquid is added during a second period of time over which the biochemical reaction is performed that does not overlap with the first period of time (i.e., the first period of time during which the first amount of liquid is added to the liquid medium). In certain embodiments, the adding step and the removing step are performed such that, between the adding step and the removing step, substantially no liquid is removed from the bioreactor via a non-evaporative pathway, and substantially no liquid is added to the bioreactor.

FIG. 1 is a schematic cross-sectional illustration of bioreactor 100, according to one set of embodiments. In FIG. 1, bioreactor 100 comprises bioreactor chamber 102. Bioreactor 100 can be configured to perform a biochemical reaction. In some embodiments, the bioreactor can be configured to grow at least one biological cell. In some such embodiments, operation of the bioreactor comprises growing at least one eukaryotic cell. For example, operating the bioreactor may comprise, in some embodiments, growing at least one animal cell, such as a mammalian cell. In some embodiments, operating the bioreactor comprises growing at least one Chinese hamster ovary (CHO) cell. In certain embodiments, the bioreactor is configured to grow an invertebrate cell (e.g., a cell from a fruit fly), a fish cell (e.g., a zebrafish cell), an amphibian cell (e.g., a frog cell), a reptile cell, a bird cell, a primate cell, a bovine cell, a horse cell, a porcine cell, a goat cell, a dog cell, a cat cell, or a cell from a rodent such as a rat or a mouse. In some embodiments, the bioreactor can be configured to grow at least one human cell. If the cell the bioreactor is configured to grow is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. While cell growth, and in particular eukaryotic cell growth, is primarily described herein, it should be understood that other types of biochemical reactions could also be performed using bioreactor 100. For example, in some embodiments, the bioreactor can be used to produce a protein.

In certain embodiments, the bioreactor contains a liquid. For example, referring back to the exemplary embodiment of FIG. 1, bioreactor chamber 102 contains a liquid 104. The liquid within the bioreactor may comprise, in certain embodiments, a cell growth medium. In embodiments in which one or more cell growth media are employed, any suitable type of medium can be used, including any common cell-growth medium containing essential amino acids and/or cofactors known to those of ordinary skill in the art. In embodiments in which the bioreactor is configured to perform other types of biochemical reactions, the liquid within the bioreactor may contain any other suitable precursor for performing the biochemical reaction.

The liquid medium within the bioreactor may occupy a relatively small volume, in certain embodiments. For example, in some embodiments, the liquid medium has a volume of less than about 50 milliliters, less than about 10 milliliters, or less than about 5 milliliters (and/or in certain embodiments, as little as 1 milliliter, 0.1 milliliters, or less). The use of small volume bioreactors can be desirable, for example, when one wishes to perform parallel analysis of a large number of bioreactor conditions while using relatively small amounts of input material (e.g., cells, growth medium, etc.). However, the use of such small volumes can present challenges. For example, accurate control of reaction conditions can be relatively difficult to achieve in such small volume reactors. As noted above, certain aspects of the present invention relate to feeding and/or sampling techniques that allow for the effective operation of bioreactors having very small volumes.

Certain embodiments relate to adding liquid to and/or removing liquid from the bioreactor such that the volume of the liquid within the bioreactor is maintained substantially constant. This can be achieved, according to certain embodiments, by adding liquid to and/or removing liquid from the bioreactor in controlled amounts such that the volume of liquid within the bioreactor does not exceed a maximum allowable value and/or does not drop below a minimum acceptable value. In certain embodiments, the bioreactor may be operated in a fed-batch mode of operation.

In some embodiments, operation of the bioreactor comprises adding a first amount of liquid to the liquid medium in the bioreactor (e.g., during the biochemical reaction). The first amount of liquid can be added to the liquid medium in the bioreactor during a first period of time over which the biochemical reaction is performed within the bioreactor. In certain embodiments, the liquid that is added to the bioreactor can be at least a portion of a makeup stream, which can be used to maintain the volume of liquid within the bioreactor within an acceptable range of volumes. In some embodiments, the liquid that is added to the liquid medium in the bioreactor comprises at least one biochemical reactant. For example, the liquid that is added to the liquid medium in the bioreactor can comprise an essential amino acid, a cofactor, and/or any other suitable reactant useful for performing a biochemical reaction. In certain embodiments, the composition of the liquid that is added to the bioreactor can be substantially the same as the composition of the liquid within the bioreactor. For example, the liquid that is added to the bioreactor may contain the same or similar growth medium as is contained within the bioreactor during operation. By adding liquid having a composition that is substantially the same as the composition of the liquid within the bioreactor, one or more properties of the liquid within the bioreactor (e.g., pH, osmolarity, nutrient concentration, etc.) can be maintained substantially constant. In other embodiments, the composition of the liquid that is added to the bioreactor may be different than the composition of the liquid medium contained within the bioreactor during operation. In some embodiments, the liquid that is added to the liquid medium in the bioreactor is not substantially pure water. For example, the liquid that is added to the liquid medium in the bioreactor may be an aqueous composition containing water and at least one other component. In some embodiments, the liquid that is added to the liquid medium in the bioreactor is a non-aqueous composition.

Operating the bioreactor may involve, in certain embodiments, removing a second amount of liquid from the liquid medium in the bioreactor (e.g., during the biochemical reaction). The second amount of liquid can be removed from the bioreactor during a second period of time over which the biochemical reaction is performed within the bioreactor. In certain embodiments, the second amount of liquid that is removed from the bioreactor comprises a product of a biochemical reaction. For example, the second amount of liquid that is removed from the bioreactor can comprise, in some embodiments, a biological cell. In some embodiments, the second amount of liquid that is removed from the bioreactor can comprise a protein. In certain embodiments, the second amount of liquid that is removed from the liquid medium in the bioreactor is not substantially pure water. For example, the liquid that is removed from the liquid medium in the bioreactor can be, in some embodiments, an aqueous composition containing water and at least one other component. In some embodiments, the liquid that is removed from the liquid medium in the bioreactor is a non-aqueous composition.

In certain embodiments, the liquid that is removed from the bioreactor may be removed as part of a sampling procedure. For example, in certain embodiments, operating the bioreactor comprises determining at least one property (e.g., pH, osmolarity, component concentration, and/or temperature) of the liquid that is removed from the bioreactor. In some embodiments, operating the bioreactor comprises altering at least one property of the bioreactor (e.g., pH and/or temperature) and/or of a liquid input stream (e.g., pH, temperature, flow rate, and/or composition) at least partially in response to the determination of the property of the liquid that is removed from the bioreactor.

Liquid can be added to and/or removed from the bioreactor via any suitable pathway. In some embodiments, adding the first amount of liquid to the liquid medium within the bioreactor comprises transporting the first amount of liquid into the bioreactor via a liquid inlet. For example, referring to FIG. 1, the first amount of liquid (and/or, subsequent amounts of liquid) can be added to bioreactor 100 via liquid inlet 114. The liquid inlet can comprise, in certain embodiments, a channel, such as a microfluidic channel. For example, referring to FIG. 1, liquid inlet 114 corresponds to a microfluidic liquid inlet channel fluidically connected to reactor chamber 102.

In some embodiments, removing the second amount of liquid from the liquid medium in the bioreactor comprises transporting the second amount of liquid out of the bioreactor via a liquid outlet. For example, referring to FIG. 1, the second amount of liquid (and/or, subsequent amounts of liquid) can be removed from bioreactor 100 via liquid outlet 115. The liquid outlet can comprise, in certain embodiments, a channel, such as a microfluidic channel. For example, referring to FIG. 1, liquid outlet 115 corresponds to a microfluidic liquid outlet channel fluidically connected to reactor chamber 102.

Transporting liquid into and/or out of the bioreactor can be achieved using any suitable method. For example, in some embodiments, a pressure gradient can be established by applying a positive pressure to the inlet of a channel using, for example, a pump, via gravity, or by any other suitable method. In some embodiments, pressure gradients within a channel can be established by applying a negative pressure to an outlet of a channel, for example, via attachment of a vacuum pump to an outlet, withdrawal of air from a syringe attached to an outlet, or by any other suitable method. Fluid transport can also be achieved using peristaltic pumping configurations, including those described elsewhere herein.

In certain embodiments, the adding and removing steps can be performed such that the volume of the liquid medium within the bioreactor remains substantially constant during the time over which the biochemical reaction (e.g., cell growth) is performed. For example, in some embodiments, during at least about 80% (or at least about 90%, at least about 95%, or at least about 99%, and/or, in certain embodiments, up to 100%) of the time over which the biochemical reaction is performed including during the adding and removing steps, the total volume of liquid within the bioreactor does not fluctuate by more than about 20% (or more than about 10%, or more than about 5%) from the average of the volume of liquid within the bioreactor. One of ordinary skill in the art would be capable of determining the average of the volume of the liquid within the bioreactor during a biochemical reaction by, for example, monitoring the volume of the liquid within the bioreactor during the time over which the biochemical reaction is performed and calculating a the average of the volume as a time-averaged value.

According to certain embodiments, the volume of the first amount of liquid that is added to the bioreactor and the volume of the second amount of liquid that is removed from the bioreactor are relatively close. In some such embodiments, removing amounts of liquid that are close in volume to the amounts of added liquid can ensure that the liquid level in the bioreactor is maintained within a desired range of volumes during operation of the bioreactor. In some embodiments, operating the bioreactor comprises adding a first amount of liquid to the bioreactor and removing a second amount of liquid from the bioreactor, wherein the second amount of liquid has a volume that is within 10% of (or within 5% of, within 1% of, and/or, in certain embodiments, substantially the same as) the volume of the first amount of liquid.

In some embodiments, the steps of adding liquid to and removing liquid from the bioreactor are performed as temporally separate steps. In certain embodiments, the step of adding the first amount of liquid is performed over a first period of time, the step of removing the second amount of liquid is performed over a second period of time, and the first and second periods of time do not substantially overlap with each other. For example, in some embodiments, the step of adding the first amount of liquid may be performed first, and after the adding step has been completed, the step of removing the second amount of liquid may be performed. In some embodiments, the step of removing the second amount of liquid may be performed first, and after the removing step has been completed, the step of adding the first amount of liquid may be performed. It should be understood, however, that separate adding and removing steps are not required in all embodiments, and that in some instances, the adding and removing steps may at least partially (or may substantially completely) overlap.

In certain embodiments, the adding step and/or the removing step are performed such that, between the adding step and the removing step, substantially no liquid is removed from the bioreactor via a non-evaporative pathway. For example, referring back to FIG. 1, in some embodiments, during operation of bioreactor 100, substantially no liquid is removed from the bioreactor via liquid outlet 115 between the adding step and the removing step. In some embodiments, the adding step and the removing step are performed such that, between the adding step and the removal step, substantially no liquid is removed from the bioreactor (e.g., via an evaporative pathway, such as through a vapor-permeable membrane, or via any other pathway).

In some embodiments, the adding step and/or the removing step are performed such that, between the adding step and the removing step, substantially no liquid is added to the bioreactor. For example, referring back to FIG. 1, in some embodiments, during operation of bioreactor 100, substantially no liquid is added to the bioreactor via liquid inlet 114 between the adding step and the removing step.

The steps of adding liquid and removing liquid can be repeated, according to certain embodiments, any number of times. In some embodiments, the steps of adding liquid and removing liquid can be repeated at least one time, at least two times, at least five times, at least ten times, or at least 100 times (and/or, in certain embodiments, up to 1,000 times, up to 10,000 times, or more) during the biochemical reaction.

In certain embodiments, the osmolarity of the liquid medium within the bioreactor is maintained within a desired range of values. Maintaining the osmolarity within a desired range can be beneficial, for example, when the bioreactor is used to grow cells that are sensitive to the concentration of salt within the liquid growth medium. For example, eukaryotic cells can be, in some instances, sensitive to the osmolarity of the liquid medium in which they are grown. In some such instances, if the osmolarity of the liquid growth medium is too high, water may flow out of the cell, which can damage the cell membrane and render it metabolically inactive. In addition, in some such instances, if the osmolarity of the liquid growth medium is too low, water may flow into the cell, which may cause the cell to burst. Eukaryotic cells can be particularly sensitive to the osmolarity of the liquid growth medium. In addition, eukaryotic cells generally require osmotic conditions that are different from (and, in many cases, harder to achieve) those required by prokaryotic cells.

In some embodiments, the osmolarity of the liquid medium within the bioreactor is maintained within a range of from about 200 osmoles per kilogram of the liquid medium to about 600 osmoles per kilogram of the liquid medium (and/or, in certain embodiments, from about 300 osmoles per kilogram of the liquid medium to about 500 osmoles per kilogram of the liquid medium). In some embodiments, during at least about 80% (or at least about 90%, at least about 95%, or at least about 99%, and/or, in certain embodiments, up to 100%) of the time over which the biochemical reaction is performed including during the adding and removing steps, the osmolarity of the liquid medium within the bioreactor is maintained within a range of from about 200 osmoles per kilogram of the liquid medium to about 600 osmoles per kilogram of the liquid medium (or, in certain embodiments, from about 300 osmoles per kilogram of the liquid medium to about 500 osmoles per kilogram of the liquid medium). In some embodiments, maintaining the osmolarity of the liquid growth medium within a desired range can be accomplished, for example, by adding liquid to the bioreactor that has an osmolarity that is within 10% of, within 5% of, within 1% of, or substantially the same as the osmolarity of the liquid within the bioreactor. For example, one can add a liquid growth medium to the bioreactor having a similar salt concentration as that of the liquid growth medium already contained in the bioreactor.

Figure 2:
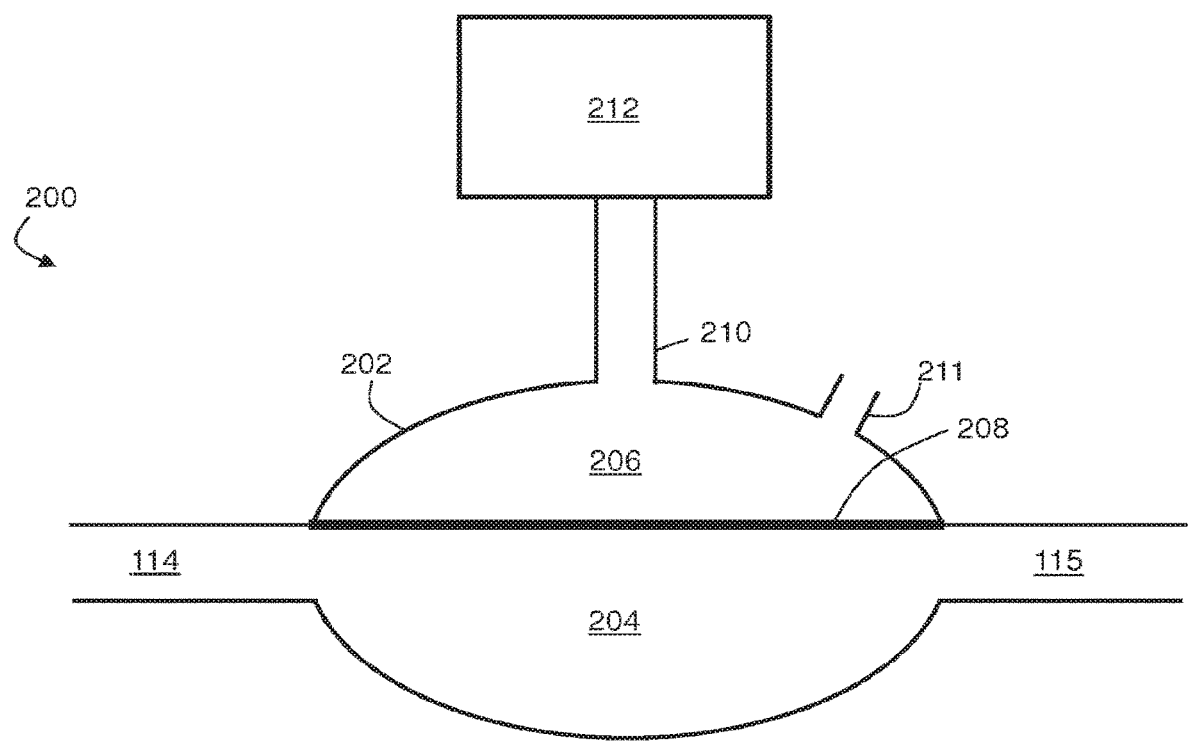
FIG. 2 is, according to certain embodiments, a cross-sectional side view schematic illustration of an exemplary reactor system.

While FIG. 1 illustrates one type of bioreactor configuration that may be employed in association with certain of the embodiments described herein, other types of bioreactors could also be used. One such example is illustrated in FIG. 2. In FIG. 2, bioreactor 200 comprises bioreactor chamber 202. Bioreactor chamber 202 can comprise a gaseous headspace 206. Gaseous headspace 206 can be positioned above liquid growth medium 204 in bioreactor chamber 202. In certain embodiments, gaseous headspace 206 and liquid growth medium 204 can be in direct contact. In such systems, interface 208 in FIG. 2 can correspond to a gas-liquid interface. In other embodiments, gaseous headspace 206 and liquid growth medium 204 are separated by a moveable wall. For example, interface 208 can correspond to a flexible membrane. In embodiments in which such flexible membranes are employed, the membrane can be permeable to at least one gas. For example, the flexible membrane can be, in certain embodiments, permeable to oxygen and/or carbon dioxide.

In certain embodiments, reactor chamber 202 comprises a first inlet 210 connecting a source 212 of gas to gaseous headspace 206. Source 212 can be any suitable source, such as a gas tank. The gas within gaseous headspace may be used to actuate the movement of interface 208 and/or to deliver gas to and/or remove gas from liquid medium 204. Source 212 can contain any suitable gas such as carbon dioxide, oxygen (which can be used to aerate liquid growth medium 204), and/or an inert gas (such as helium or argon, which might be used to actuate interface 208 to produce mixing within liquid growth medium 204, as described in more detail elsewhere). Optionally, reactor chamber 202 can comprise outlet 211, which can be used to transport gas out of gaseous headspace 206. Reactors employing arrangements similar to those described with respect to FIG. 2 are described, for example, in U.S. Patent Publication No. 2013/0084622 by Ram et al., filed Sep. 30, 2011, and entitled "Device and Method for Continuous Cell Culture and Other Reactions" and U.S. Patent Application Publication No. 2005/0106045 by Lee, filed Nov. 18, 2003, and entitled "Peristaltic Mixing and Oxygenation System," each of which is incorporated herein by reference in its entirety for all purposes.

Figure 3A:
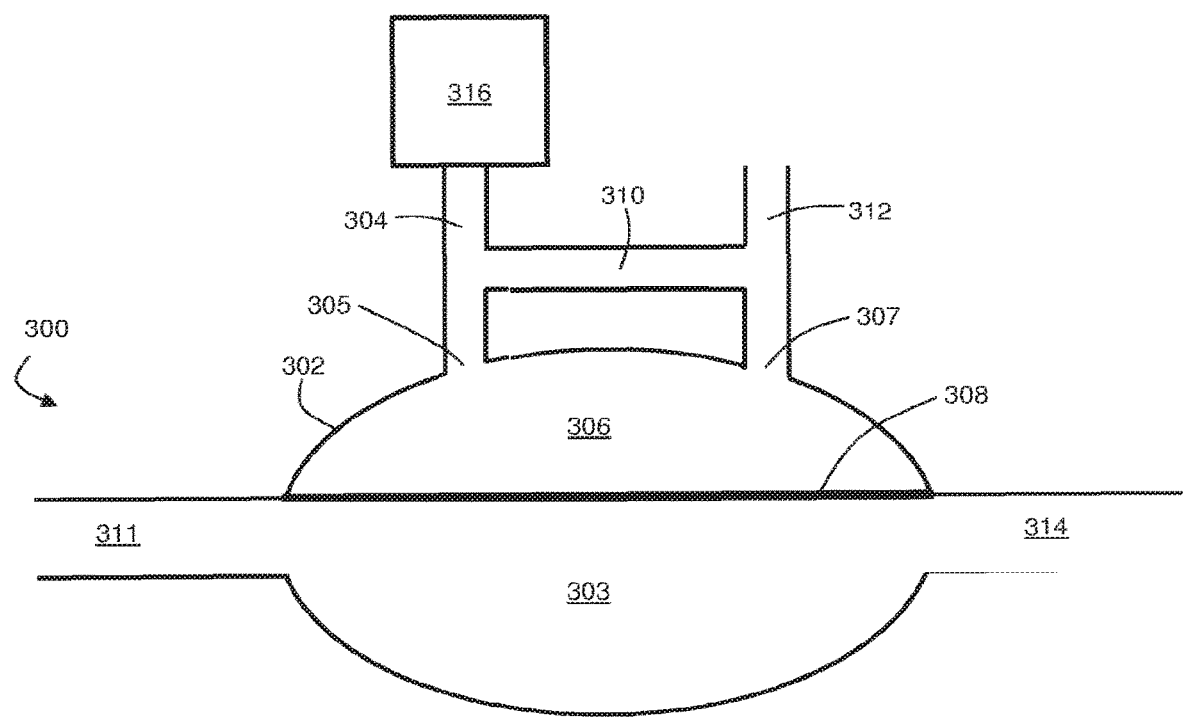
FIGS. 3A-3C are cross-sectional side view schematic illustrations of a reactor chamber and a mode of operating the same, according to some embodiments.
Figure 3B:
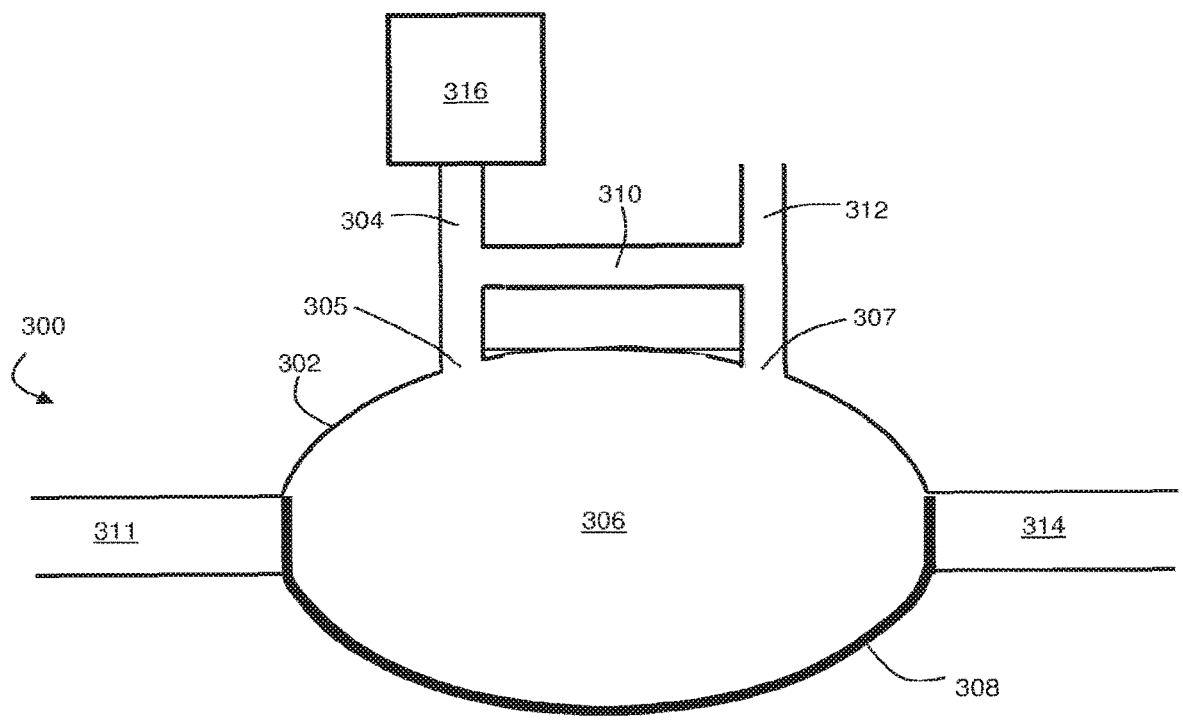
Figure 3C:
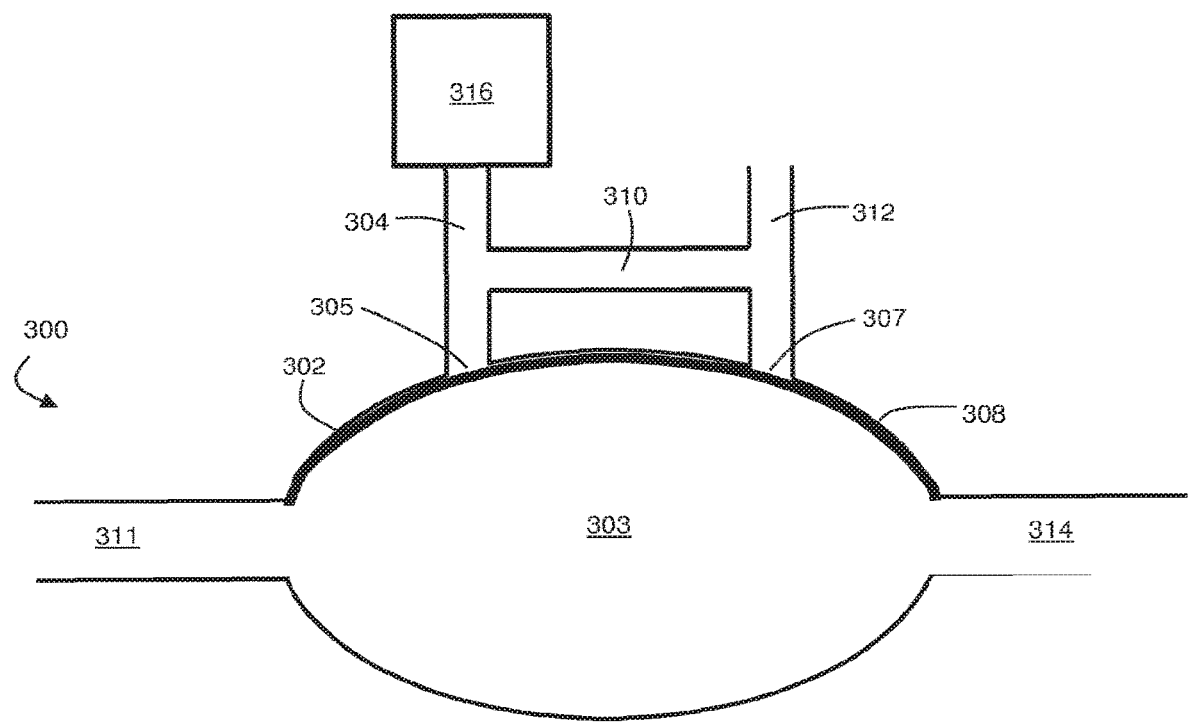

FIGS. 3A-3C are cross-sectional schematic illustrations outlining how fluid can be transported by deflecting a moveable wall into and out of a liquid sub-chamber of a reactor chamber. In FIGS. 3A-3C, reactor system 300 comprises reactor chamber 302. In certain embodiments, reactor chamber 302 in FIGS. 3A-3C corresponds to reactor chamber 202 in FIG. 2. Reactor chamber 302 can comprise a liquid sub-chamber 303. Liquid sub-chamber 303 can be configured to contain a liquid growth medium including at least one biological cell. Reactor chamber 302 can comprise, in certain embodiments, gas sub-chamber 306. Gas sub-chamber 306 can be configured to contain a gaseous headspace above the liquid growth medium within liquid sub-chamber 303.

Reactor chamber 302 can also comprise a moveable wall 308, which can separate liquid sub-chamber 303 from gas sub-chamber 306. Moveable wall 308 can comprise, for example, a flexible membrane. In certain embodiments, the moveable wall is formed of a medium that is permeable to at least one gas (i.e., a gas-permeable medium). In certain embodiments, for example, moveable wall can be permeable to oxygen gas and/or carbon dioxide gas. In such embodiments in which moveable wall 308 is permeable to a gas (e.g., oxygen and/or carbon dioxide), the gas within gas sub-chamber 306 can be transported to liquid sub-chamber 303, or vice versa. Such transport can be useful, for example, to transport oxygen gas into a liquid medium within liquid sub-chamber 303 and/or control pH by transporting carbon dioxide into or out of liquid sub-chamber 303.

Reactor system 300 can comprise, in certain embodiments, a gas inlet conduit 304, which can be configured to transport gas into gas sub-chamber 306. Gas inlet conduit 304 in FIGS. 3A-3C can correspond to the gas inlet conduit 210 illustrated in FIG. 2, in certain embodiments. The gas that is transported into gas sub-chamber 306 can originate from, for example, gas source 316. Any suitable source of gas can be used as gas source 316, such as gas cylinders. In certain embodiments, gas source 316 is a source of oxygen and/or carbon dioxide.

In some embodiments, reactor system 300 comprises gas outlet conduit 312 configured to transport gas out of gas sub-chamber 306. Gas outlet conduit 312 in FIGS. 3A-3C can correspond to the gas outlet conduit 211 illustrated in FIG. 2, in certain embodiments. In some embodiments, reactor system 300 comprises gas bypass conduit 310 connecting gas inlet conduit 304 to gas outlet conduit 312. Gas bypass conduit 310 can be configured such that it is external to reactor chamber 302, in certain embodiments. Reactor system 300 can also comprise, in certain embodiments, a liquid inlet conduit 311 and a liquid outlet conduit 314.

In certain embodiments, moveable wall 308 can be actuated such that the volumes of liquid sub-chamber 303 and gas sub-chamber 306 are modified. For example, certain embodiments involve transporting a gas from gas source 316 through gas inlet conduit 304 to gas sub-chamber 306 to deform moveable wall 308. Deformation of moveable wall 308 can be achieved, for example, by configuring reactor 300 such that gas sub-chamber 306 is pressurized when gas is transported into gas sub-chamber 306. Such pressurization can be achieved, for example, by restricting the flow of gas out of gas outlet conduit 312 (e.g., using valves or other appropriate flow restriction mechanisms) while gas is being supplied to gas sub-chamber 306.

In certain embodiments, deforming moveable wall 308 can result in liquid being at least partially evacuated from liquid sub-chamber 303. For example, in FIG. 3B, moveable wall 308 has been deformed such that substantially all of the liquid within liquid sub-chamber 303 has been evacuated from reactor chamber 302. Such operation can be used to transport the liquid within liquid sub-chamber 303 to other liquid sub-chambers in other reactors, as illustrated, for example, in FIG. 4, described in more detail below.

In certain embodiments, after at least a portion of the liquid within liquid sub-chamber 303 has been removed from liquid sub-chamber 303, the supply of the gas to gas sub-chamber 306 can be reduced such that moveable wall 308 returns toward its original position (e.g., the position illustrated in FIG. 3A). In certain embodiments, moveable wall 308 will be deflected such that at least a portion of the gas within gas sub-chamber 306 is removed from the gas sub-chamber. Such gas might be removed, for example, if liquid enters liquid sub-chamber 303 from liquid inlet conduit 311, for example, from another upstream reactor, as described in more detail below.

Certain embodiments include the step of supplying gas from gas source 316 to gas sub-chamber 306 at least a second time to deform moveable wall 308 such that liquid is at least partially removed from liquid sub-chamber 303. When such gas introduction steps are performed repeatedly, moveable wall 308 can act as part of a pumping mechanism, transporting liquid into and out of liquid sub-chamber 303. Such operation is described in detail in U.S. Patent Publication No. 2013/0084622 by Ram et al, filed Sep. 30, 2011, and entitled "Device and Method for Continuous Cell Culture and Other Reactions," which is incorporated herein by reference in its entirety for all purposes.

In certain embodiments in which gas is transported into gas sub-chamber 306 multiple times, gas can be transporting from the gas source through gas bypass conduit 310. Transporting gas through gas bypass conduit 310 can be performed to remove liquid from gas inlet conduit 304 without transporting the liquid to gas sub-chamber 306. For example, in certain embodiments, a first valve between gas bypass conduit 310 and gas inlet 305 can be closed and a second valve between gas bypass conduit 310 and gas outlet 307 can be closed (and any valves within gas bypass conduit 310 can be opened) such that, when gas is transported through gas inlet conduit 304, the gas is re-routed through gas bypass conduit 310, and subsequently out gas outlet conduit 312. Such operation can serve to flush any unwanted condensed liquid out of the gas inlet conduit, which can improve the performance of the gas supply methods described elsewhere herein.

Figure 4:
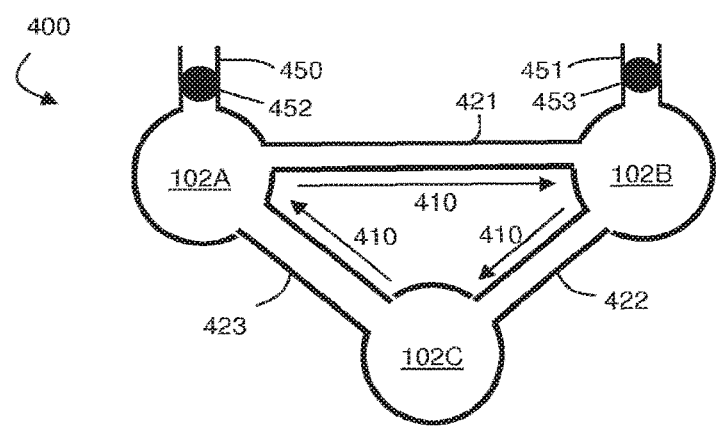
FIG. 4 is a bottom-view cross sectional schematic illustration of a reactor system including a plurality of reactor chambers arranged in series, according to one set of embodiments.

In some embodiments, multiple sets of reactor chambers can be arranged (e.g., in series) such that fluidic mixing is achieved along one or more fluidic pathways. FIG. 4 is a bottom view, cross-sectional schematic diagram illustrating the liquid flow paths that can be used to establish mixing between multiple reactor chambers 102A-C connected in series, as described in U.S. Patent Publication No. 2013/0084622 by Ram et al, filed Sep. 30, 2011, and entitled "Device and Method for Continuous Cell Culture and Other Reactions," which is incorporated herein by reference in its entirety for all purposes.

In FIG. 4, reactor system 400 includes a first fluidic pathway indicated by arrows 410. The first fluidic pathway can include a first reactor chamber 102A, a second reactor chamber 102B, and a third reactor chamber 102C. Reactor system 400 also includes conduits 421, 422, and 423, which can correspond to liquid inlet and/or liquid outlet conduits for reactor chambers 102A-C. For example, in FIG. 4, conduit 421 is a liquid inlet conduit for reactor chamber 102B and a liquid outlet conduit for reactor chamber 102A; conduit 422 is a liquid inlet conduit for reactor chamber 102C and a liquid outlet conduit for reactor chamber 102B; and conduit 423 is a liquid inlet conduit for reactor chamber 102A and a liquid outlet conduit for reactor chamber 102C. Of course, the flow of liquid can also be reversed such that conduits 421, 422, and 423 assume opposite roles with respect to each of reactor chambers 102A-C.

Reactor system 400 can also include a liquid input conduit 450 and a liquid output conduit 451, which can be used to transport liquid into and out of the liquid sub-chambers within reactor chambers 102A, 102B, and 102C. Valve 452 may be located in liquid input conduit 450, and valve 453 may be located in liquid output conduit 451 to inhibit or prevent to the flow of liquid out of the mixing system during operation.

In certain embodiments, the moveable walls of reactor chambers 102A-C can be actuated to transport liquid along fluidic pathway 410 (and/or along a fluidic pathway in a direction opposite pathway 410). This can be achieved, for example, by sequentially actuating the moveable walls within reactor chambers 102A-C such that liquid is transported in a controlled direction. In some embodiments, each of reactor chambers 102A-C can be configured such that they are each able to assume a closed position wherein moveable wall 308 is strained such that the volume of the liquid sub-chamber is reduced, for example, as illustrated in FIG. 3B. Peristaltic mixing can be achieved, for example, by actuating reactor chambers 102A-C such that their operating states alternate between open (FIG. 3A or FIG. 3C) and closed (FIG. 3B) configurations. In some embodiments, three patterns may be employed to achieve peristaltic pumping: a first pattern in which the liquid sub-chamber of reactor chamber 102A is closed and the liquid sub-chambers within reactor chambers 102B and 102C are open; a second pattern in which the liquid sub-chamber of reactor chamber 102B is closed and the liquid sub-chambers within reactor chambers 102A and 102C are open; and a third pattern in which the liquid sub-chamber of reactor chamber 102C is closed and the liquid sub-chambers within reactor chambers 102A and 102B are open. By transitioning among these three patterns (e.g., changing from the first pattern to the second pattern, from the second pattern to the third pattern, and from the third pattern to the first pattern, etc.) liquid can be transported among reactor chambers 102A-C in a clockwise direction (as illustrated in FIG. 4). Of course, by re-arranging the order in which the patterns occur (e.g., by changing from the first pattern to the third pattern, from the third pattern to the second pattern, and from the second pattern to the first pattern, etc.), liquid can be transported in the counter-clockwise direction as well.

The bioreactors described herein may be manufactured using a variety of suitable techniques. In some embodiments, the bioreactors are fabricated using standard microfabrication techniques. Such techniques may involve various film deposition processes (such as spin coating, atomic layer deposition, sputtering, thermal evaporation, electroplating, electroless plating, and chemical vapor deposition), laser fabrication processes, photolithographic techniques, etching methods including wet chemical or plasma processes, and the like. In some embodiments, the bioreactors can be fabricated using micromachining techniques. In certain embodiments, the bioreactors can be fabricated using molding techniques.

The systems described herein may be microfluidic, in some embodiments, although the invention is not limited to microfluidic systems and may relate to other types of fluidic systems. "Microfluidic," as used herein, refers to a device, apparatus or system including at least one fluid channel having a cross-sectional dimension of less than about 1 mm. A "microfluidic channel," as used herein, is a channel meeting these criteria. The "cross-sectional dimension" (e.g., a diameter) of the channel is measured perpendicular to the direction of fluid flow. In some embodiments, the devices described herein include at least one channel having a maximum cross-sectional dimension of less than about 500 micrometers, less than 200 micrometers, less than about 100 micrometers, less than 50 micrometers, or less than about 25 micrometers.

The following examples are intended to illustrate certain embodiments of the present invention, but do not exemplify the full scope of the invention.

EXAMPLE 1

This example describes the operation of a bioreactor in which the liquid volume within the reactor is maintained within a desired range while liquid is added to and removed from the bioreactor.

Bench top bioreactors are the standards for scale down models of industrial bioreactors at a scale of 1,000-10,000 times smaller than industrial bioreactors. Since volume and surface area scale differently with length, the physical and chemical environment experienced by the cells even in bench top bioreactors that are geometrically identical to industrial bioreactors will be different. The physical and chemical environment of the cells can strongly affect the cells' physiology and productivity and hence should be maintained constant or within the limits of critical values during scaling. First, the gas transfer rate of $O_2$ and $CO_2$ should be sufficiently high so that the dissolved oxygen level remains above the oxygen uptake rate of the cells and waste gas like carbon dioxide are efficiently removed. Secondly, the maximum shear rate experienced by the cells should remain the same or below the critical value that affects productivity during the scaling. This can be especially important for mammalian cells like CHO due to their shear sensitivity. The circulation time is also an important parameter since it affects the frequency at which the cells experience high shear. The repeated deformation of the endoplasmic reticulum has been reported to affect protein glycosylation. Bioreactors with different chamber volumes will have very different circulation time before the cells circulate back to the tip of the impeller and hence, some bench top bioreactors are equipped with a circulation line that allows the physical environment of the cells to mimic the circulation time seen in large industrial scale bioreactors. On the other hand, the mixing rate of the micro-bioreactor must be sufficiently fast and uniform so that there is no region in the culture where the cell is nutrient starved or have a large concentration gradient. When designing scale down models of bioreactors, the energy dissipation rate should be maintained substantially constant so that the transfer of internal energy to the cell remains substantially constant.

Micro-bioreactors can be instrumented with online sensors like pH, dissolved oxygen (DO), dissolved carbon dioxide ($DCO_2$) and optical density (OD) sensors. However, in order to fully characterize the condition of the cell culture, offline sampling to monitor other important culture parameters is generally desirable. Offline sampling for cell viability measurements can be used to ensure that the cell viability remains high during the culture, since CHO cells are very fragile. It would be desirable if cell viability could be measured in real-time as an online sensor in the micro-bioreactor. For fed-batch cultures, where glucose is fed to the cells in the middle of the culture, osmolarity is generally an important parameter and can generally only be measured offline since it typically involves freezing the sample to determine the freezing point. A high osmolarity can repress cell metabolism and cause cell shrinkage. Next, to monitor cell health and productivity, it is desirable to measure (by conventional methods) the concentration of metabolites and product titer in the culture medium. These are generally measured offline since these measurements involve the addition of reagents. In some instances, online sensors need to be recalibrated to account for any drifts during the culture, and hence, such measurements might need to be performed offline using a blood gas analyzer as a standard for comparison. Furthermore, end point measurements may be needed to ensure that the final products have the right glycosylation, are not fragmented and have the right peptide groups and function. Generally, the volume of the bioreactor will need to be sufficiently large to allow one to conduct these offline samples (and also for the end point protein titer and quality analysis) in order for these micro-bioreactors to function as well as bench top bioreactors.

Exemplary sample volume requirements for various commercially available units are summarized in Table 1.

TABLE 1

Offline sampling volume requirements for various commercial analyzers.

| No | Instrument | Required Volume | Dilution | Sample Volume |
|---|---|---|---|---|
| | Cell Viability Measurements (5 Samples) | | | |
| 1 | Hemacytometer | 25 µL | 1:1-1:10 | 2.5-25 µL |
| 2 | Cedex HiRes Analyzer (Innovatis) | 300 µL | 1:10 | 30 µL |
| 3 | Vi-CELL (Beckman Coulter) | 500 µL | 1:10 | 50 µL |
| 4 | Countess (Invitrogen) | 10 µL | 1:1-1:10 | 1-10 µL |
| | Blood Gas Analyzer (2 Samples) | | | |
| 1 | Cobas b 221 (Roche) | 50 µL | 1:1 | 50 µL |
| 2 | Ciba Corning 840 (Corning) | 45 µL | 1:1 | 45 µL |
| | Osmometer (5 Samples) | | | |
| 1 | Osmomat Auto (Gonotec) | 50 µL | 1:1 | 50 µL |
| 2 | 5010 Osmette III (PSi) | 10 µL | 1:1 | 10 µL |
| 3 | Model 20G Osmometer (Advanced Instruments) | 20 µL | 1:1 | 20 µL |
| | Metabolites and Protein Titer (5 Samples) | | | |
| 1 | RX Daytona (Randox) | 150 µL | 1:2 | 75 µL |
| 2 | YSI 2700 Select (metabolites only) (YSI) | 100 µL | 1:2 | 50 µL |
| 3 | Octet QK (titer only) (Fortebio) | 100 µL | 1:2 | 50 µL |

Since the samples for these instruments are typically taken from shake flasks and large scale bioreactors, the recommended sample volumes for these instruments can be rather large. For micro-bioreactors, dilutions of the samples may be necessary to make up for the large volume required, since microbioreactors tend to have small working volumes. For cell viability measurements, hemacytometer measurements or manual counting under the optical microscope requires sample volume simply because only a small number of cells are counted, typically around 500 cells per hemacytometer. Statistically, counting 1,000 cells would mean that the measured viability would lie within ±5% of the actual viability value of the population for 95% of the samples. If the hemacytometer counting were performed twice per measurement, an accuracy of ±5% could be achieved. However, to obtain a better accuracy, automated cell counting methods, for example the Cedex HiRes, Vi-CELL and Countess Analyzers, are generally used. The Cedex HiRes and Vi-CELL requires 300-500 microliters of sample volume and allow the user to select the number of images they want counted from the sample. The larger the number of images counted, the smaller the error, but the image processing will be time-consuming. Dilutions of up to 10 times are common when measuring samples with high cell density (e.g., about $10^8$ cells/mL). The measurable cell densities are between $10^4$ and $10^9$ cells/mL and hence, even at an incubation density of $2\times10^5$ cells/mL, a dilution of 10 times will still be within the measurement range. Since most users do not utilize all the images, a part of the sample will be discarded without being counted. This is one reason why not all automated cell counting machines require such a large volume. Countess, for example, requires only a 10 microliter sample volume and hence can be used without requiring any dilution except for high cell density cultures.

Other measurements that may be taken include offline pH, dissolved oxygen (DO), and/or dissolved carbon dioxide ($DCO_2$) measurements, which can be performed using a blood gas analyzer. Since dissolved gas levels can change when the sample is removed from the environment of the growth chamber of the bioreactor, this measurement should generally be performed as fast as possible to prevent any degassing. Hence, the samples for the blood gas analyzer cannot generally be diluted. The recommended sample volumes for two commercial blood gas analyzers are shown in Table 1. The samples for offline osmolarity measurements using a freezing point osmometer also generally cannot be diluted because osmolarity is not a linear function of concentration for most biological fluids. A freezing point osmometer operates by measuring the depression of the freezing temperature due a change in chemical potential from the presence of solutes in the solution. The sample size can be controlled by the size of the cooling chamber and temperature probe. From Table 1, one can see a wide range in recommended sample volumes for the freezing point osmometer. Another offline measurement that can be performed is the measurement of the concentration of metabolites and product titer. The RX Daytona and YSI 2700 listed in Table 1 utilizes a pipette to draw out a fixed volume of samples to mix with different reagents that tests the different components in the sample. The RX Daytona can measure concentrations of glucose, glutamine, glutamate, lactate, ammonia and immunoglobulin G (IgG) requiring only 57 microliters of sample volume for the reagents. However, since the machine dips an automated pipette into a tube to draw out the required volume, the sample volume required also depends on the depth of the pipette in the tube. It is believed that the minimum sample volume at the operating height for the automated pipette is 150 microliters. The sample can be diluted 2 fold to reduce the sample volume needed, and it is believed that any further dilution would result in the glutamine concentration dropping below the measurement range for CHO media supplied with glutamate since glutamine will only be synthesized by the cells as needed. For the YSI 2700 analyzer, which measures the concentration of glucose, glutamate, glutamine and lactate, the pipetted volume is 25 microliters but the minimum sample volume needed for the operation of the machine is 100 microliters. The YSI Analyzer is generally supplemented with the Octet QK for product titer measurements, requiring a sample volume of 100 microliters. The recommended dilutions and final sample volume for each measurement are listed in Table 1 together with the total number of offline samples needed for each parameter per 14 day CHO cell culture. From Table 1, it is estimated that the total volume removed for offline sampling is approximately 650-1,000 microliters, depending on which instruments are used.

For the end point analysis, Table 2 shows the protein weight needed for the different downstream analysis of protein titer and quality.

TABLE 2

Downstream processing sampling volume requirements.

| No | Measurement | Minimum Weight | Volume (700 mg/L) | Volume (500 mg/L) |
|---|---|---|---|---|
| 1 | SEC (Size Fragmentation) | 20 µg | 30 µL | 60 µL |
| 2 | SDS-PAGE (Electrophoretic Fractionation) | 4 µg | 10 µL | 20 µL |
| 3 | Protein A HPLC (Purification) | 20 µg | 30 µL | 60 µL |
| 4 | HPAEC-PAD (Glycosylation) | 200 µg | 300 µL | 600 µL |
| 5 | WCX (Separation) | 20 µg | 30 µL | 60 µL |
|  | Total | 264 µg | 400 µL | 800 µL |

The sample volume needed for downstream analysis are shown in Table 2 for a product titer of 700 mg/L and 350 mg/L. The total volume needed for the end point analysis is between 400-800 microliters. In order for the micro-bioreactor to provide sufficient sample volume for offline and downstream analysis, the working volume of the micro-bioreactor should generally be 2 mL or higher.

Maintaining high cell viability in the CHO cell population is an important first step before any experiments on CHO cells can be performed, be it in a micro-scale environment or a large scale environment. In large scale environments, offline sampling is often performed to monitor CHO cell population viability via a cell counting method either optically with exclusion dyes or electrically using a Coulter counter. Since micro-bioreactors typically have cell suspension volumes between 10 nL to 1 mL, offline cell counting methods, typically requiring 20 L of sample each time, would significantly decrease the cell culture volume over a the culture period (typically 10 days). For micro-bioreactors, an online method is preferred for cell viability monitoring due to the small volume of the growth chamber. On the other hand, the higher data density of online sensors would be an added advantage for research based studies in microenvironments. Since the sensors will be in contact with the cell suspension, there are very stringent requirements on the types of sensors that can be utilized for online cell physiology monitoring. First, the online sensing method should be able to perform its measurement without a affecting cell viability, productivity, and physiological state. With live cells, the conditions of the media will also change over time due to cell metabolism, hence a good online sensor must also be able to work reliably even under changing media conditions. Additionally, the sensor should also be sterile and non-toxic during the entire duration of the experiment and be compatible with common sterilization methods without compromising the sensor's physical or chemical conditions. Dielectric spectroscopy (DS) for online cell viability monitoring can be particularly useful, in certain cases, because it is label-free, scalable to micro-scale systems and compatible with most sterilization methods.

Figure 5:
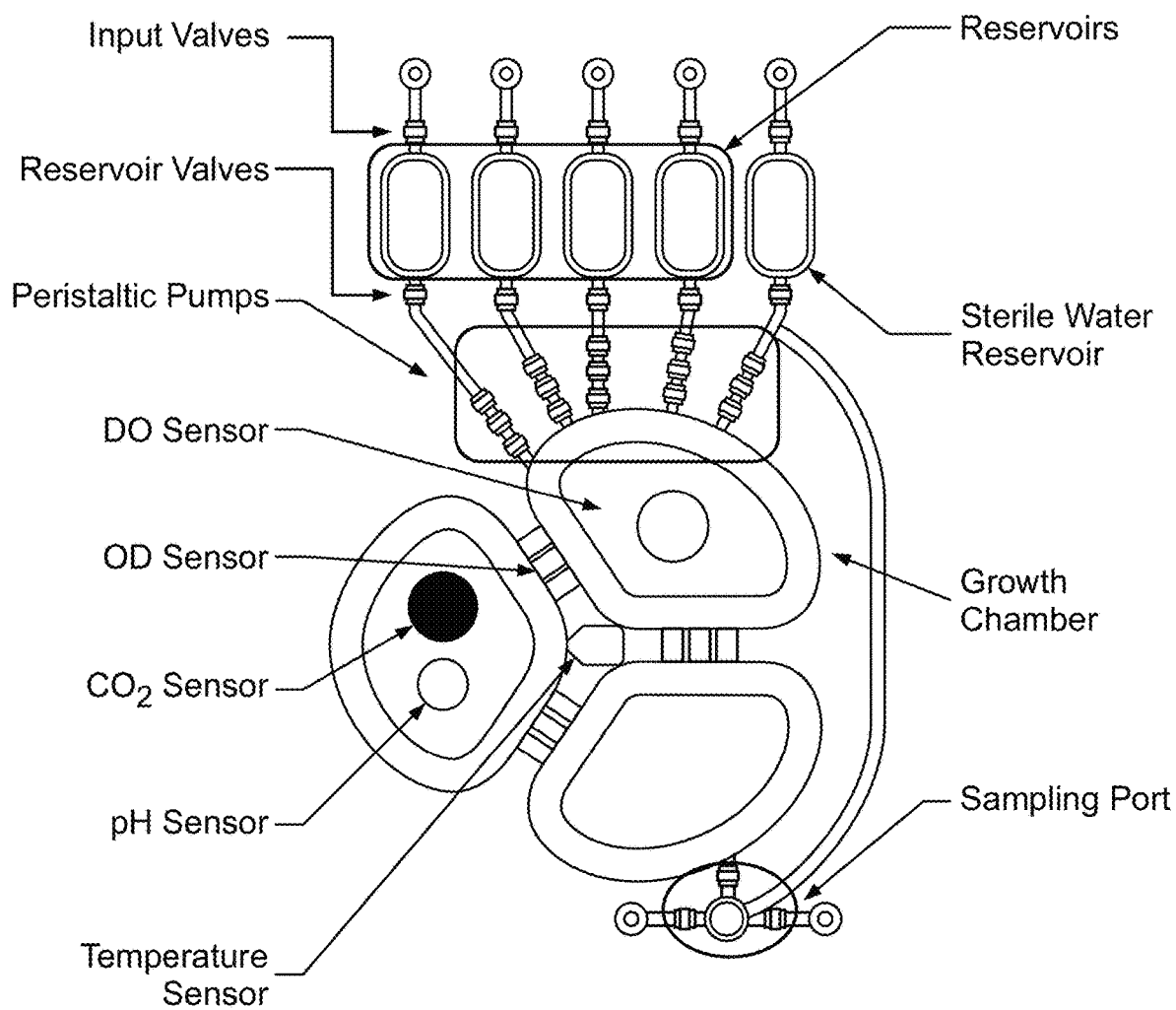
FIG. 5 is an exemplary top-view schematic illustration of a micro-bioreactor, according to one set of embodiments.

A new reactor design, referred to in this example as the Resistive Evaporation Compensated Actuator (RECA) micro-bioreactor, which is illustrated in FIG. 5, has been developed for culturing cells, including CHO cells. The reactor includes 5 reservoirs for injections, including one containing sterile water for evaporation compensation. The other four reservoirs can be used for Sodium Bicarbonate ($NaHCO_3$) base injections, feed, and other necessary supplements. Injection can be performed by a peristaltic pump actuated through the PDMS membrane sequentially pushing a plug of fluid into the growth chamber. In this example, the growth chamber has a volume of 2 milliliters. Uniform mixing can be obtained by pushing fluids through small channels connecting the three growth chambers, each having a volume of 1 milliliter. There is also a 10 microliter reservoir for sampling located after the growth chamber. The sampling can be performed via peristaltic pumping of 10 microliter plugs. Besides the connection to the growth chamber, the sample reservoir is also connected via a channel to the sterile water line and a clean air line. Air can be injected through the sample reservoir to eject any remaining sample into the sampling container (e.g. an Eppendorf tube), and water can be injected after that to clean the sample reservoir and remove any cell culture or cells remaining. Clean air can then be sent through the reservoir to dry the chambers so that there is no water left to dilute the next sample. This process can be repeated after each sampling step.

Figure 6:
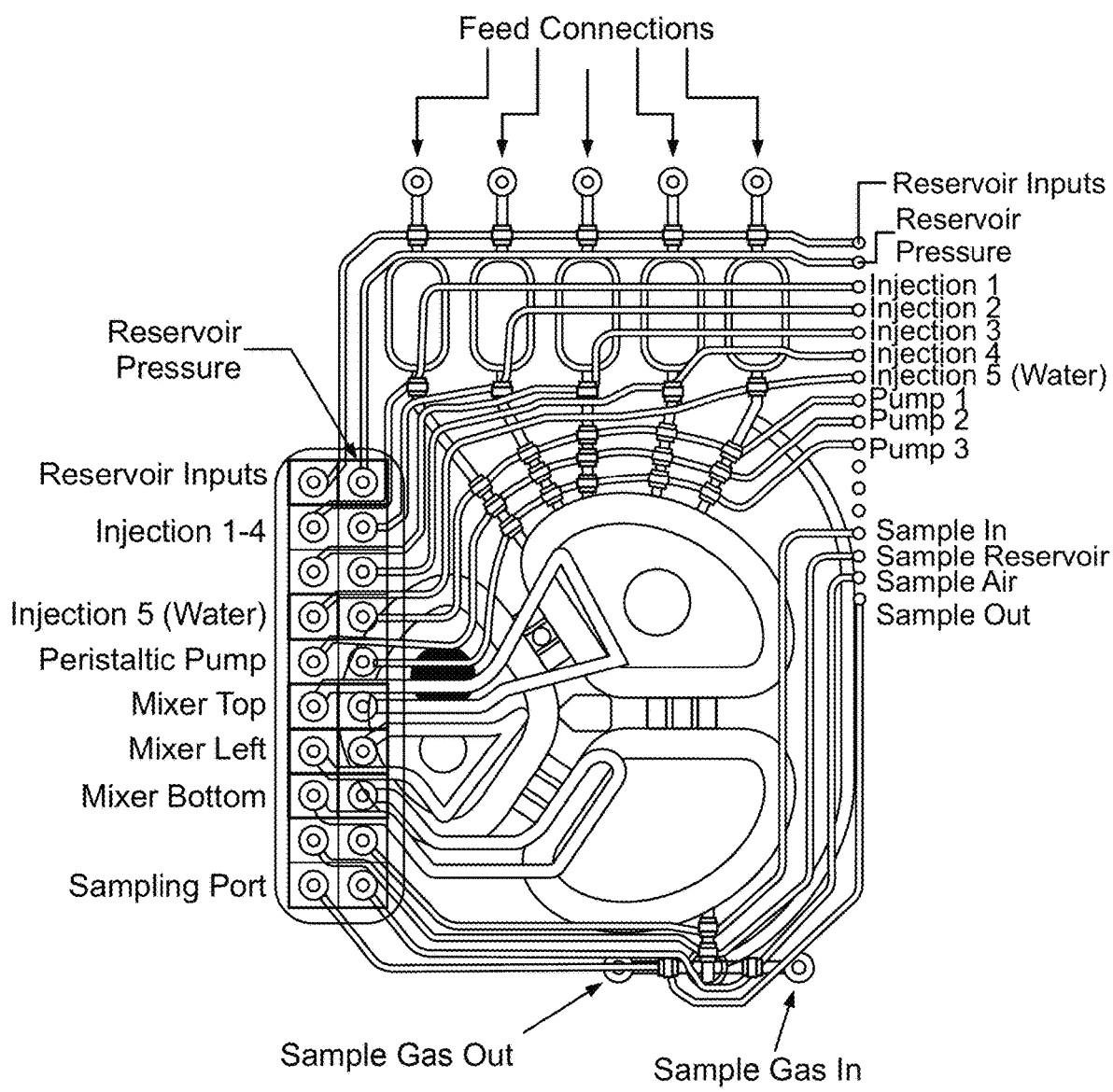
FIG. 6 is, according to certain embodiments, a top-view schematic illustration of the connectivity between the bioreactor and a gas manifold.

The connections from the RECA micro-bioreactor to the gas manifold are shown in FIG. 6. All reservoir input valves can share the same gas line since it is unnecessary to individually control each input valve. The reservoir pressure can be set to be 1.5 psi ($1.03 \times 10^5$ Pa), which is lower than that of the mixing pressure of 3 psi ($2.06 \times 10^5$ Pa). The reservoir pressure can be used to ensure that the input to the peristaltic pumps sees the same pressure and is unaffected by external hydrostatic pressure to ensure consistent pumping volume. The output of the reservoir, i.e. the injection valves, can be individually controlled by separate gas lines because these are the valves that determine which feed lines are being injected into the growth chamber. Next are the gas lines that control the peristaltic pumps. The mixers can have a separate input and output line in order to allow flushing of water condensation on the mixer lines, since the air coming into the mixer can be humidified to reduce evaporation of the growth culture. The growth chambers of the micro-bioreactor have large surface to volume ratios and hence, the evaporation rates are generally larger than that for larger bioreactors. Moreover, all three mixer gas lines can be designed to have the same resistance, to ensure an even mixing rate in the 3 growth chambers. The mixer gas lines can be made wider than the rest of the lines because the air is humidified, and any condensation might clog the lines if the resistance is too high. The last air lines control the valves to the sampling port. The sampling port consists of a 10 microliter sample reservoir and valves to control sampling and automated cleaning of the sampling port. The holes in the top left corner can be sealed with a polycarbonate cover and taped with double sided tape. The air lines can be connected through a group of 20 barbs located on the left bottom corner of the chip to the gas manifold.

Figure 7:
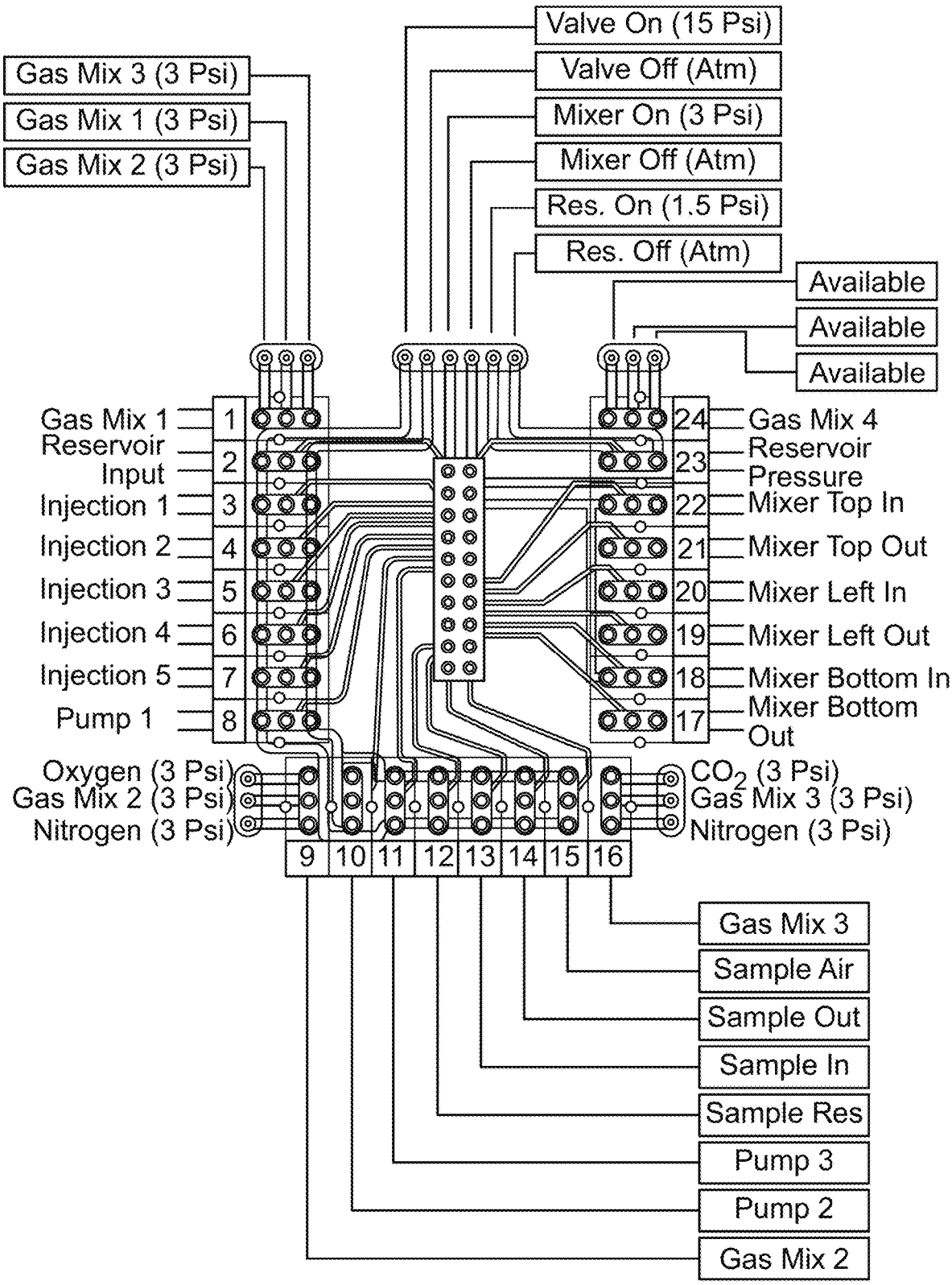
FIG. 7 is a schematic illustration of an exemplary gas manifold, according to some embodiments.

A gas manifold can be used to connect the solenoid valves to the air lines of the micro-bioreactor. The design of the gas manifold is shown in FIG. 7. The manifold in this example has 3 layers. The barb connectors to the micro-bioreactor are situated in the center of the top layer of the manifold. The middle layer routes the output of the solenoid valves to the barb connectors that connects the manifold to the micro-bioreactor. The bottom layer routes the main air lines to the inputs of the solenoid valves. FIG. 8 lists all the valves with their numbers as shown in FIG. 7 and the gas connections for easier referencing. In the table, NO stands for Normally Open and NC stands for Normally Closed. The selection of which gas lines is normally open or normally closed can be selected to be the most common state of the valve, so that more often than not, the valve is inactive, to save energy consumption. In particular, Valve 10 (Pump 2) can be set to "off" normally while all the rest of the valves are set to "on" normally. There are also 4 gas mixer solenoid valves besides the solenoid valves needed for mixing and valving on the micro-bioreactor. Control of carbon dioxide ($CO_2$) gas concentration vs. nitrogen ($N_2$) gas can be achieved by changing the duty cycle of Gas Mix 3 solenoid valve. Oxygen ($O_2$) gas concentration can be controlled via Gas Mix 2 via the same strategy. Then the two outputs can be mixed together in a 50-50 duty cycle using Gas Mix 1. Gas Mix 4 is available for use if any extra valving is needed.

Figure 9:
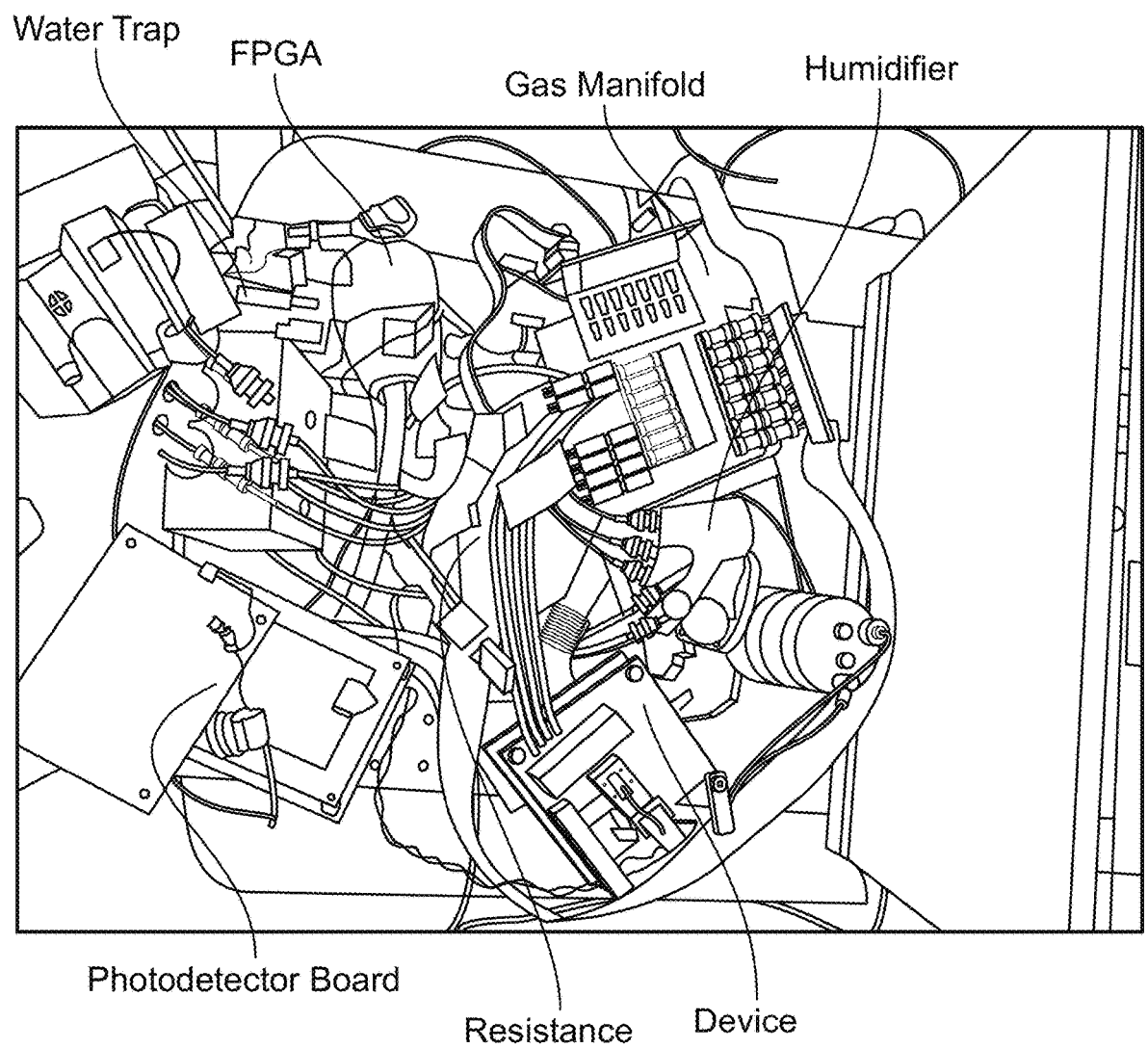
FIG. 9 is a photograph of an exemplary bioreactor system, according to certain embodiments.

The complete setup is shown in FIG. 9. A laptop can be used to control a Field-programmable Gate Array (FPGA) board, which can control the solenoid boards, the heater board, and photo-detector board. Air lines can be connected to a pressure regulator before being connected to the gas manifold. From the gas manifold, the valve lines can be connected directly to the micro-bioreactor. The mixer in lines are connected first through an air resistance line, followed by a 45° C. local humidifier before reaching the micro-bioreactor. The mixer output lines from the micro-bioreactor are connected to the water trap, then to the air resistance lines and then only to the gas manifold.

Offline sampling of the bioreactor, if not compensated for, could cause the working volume of the bioreactor to be irregular throughout the culture. In addition, for fed-batch cultures where extra feed is injected on certain days into the microbioreactor, in some cases the volume of the liquid within the bioreactor could exceed the designed working volume. The day to day volume variation expected for a batch and fed-batch 2 mL working volume CHO culture is summarized in Table 3.

TABLE 3

Day to day working volume of the RECA bioreactor for various operating schemes. All volumes are shown in microliters.

| | 2 mL Batch | | 2 mL Fed-Batch | | | | | | |
|---|---|---|---|---|---|---|---|---|---|
| | Normal | | Normal | | | Over Sample | | | |
| Day | Samp. | Total | Add | Samp. | Total | Add | Samp. | Over | Total |
| 0 | 0 | 2000 | 0 | 0 | 2000 | 0 | 0 | 0 | 2000 |
| 1 | 0 | 2000 | 200 | 0 | 2200 | 200 | 0 | 200 | 2000 |
| 2 | 0 | 2000 | 0 | 0 | 2200 | 0 | 0 | 0 | 2000 |
| 3 | 155 | 1845 | 220 | 155 | 2265 | 200 | 155 | 45 | 2000 |
| 4 | 0 | 1845 | 0 | 0 | 2265 | 0 | 0 | 0 | 2000 |
| 5 | 0 | 1845 | 227 | 0 | 2492 | 200 | 0 | 200 | 2000 |
| 6 | 155 | 1690 | 0 | 155 | 2337 | 0 | 155 | 0 | 1845 |
| 7 | 50 | 1640 | 234 | 50 | 2520 | 185 | 50 | 0 | 1980 |
| 8 | 0 | 1640 | 0 | 0 | 2520 | 0 | 0 | 0 | 1980 |
| 9 | 155 | 1485 | 252 | 155 | 2617 | 198 | 155 | 23 | 2000 |
| 10 | 0 | 1485 | 0 | 0 | 2617 | 0 | 0 | 0 | 2000 |
| 11 | 0 | 1485 | 0 | 0 | 2617 | 0 | 0 | 0 | 2000 |
| 12 | 80 | 1405 | 0 | 80 | 2537 | 0 | 80 | 0 | 1920 |
| 13 | 75 | 1330 | 0 | 75 | 2462 | 0 | 75 | 0 | 1845 |
| 14 | 205 | 1125 | 0 | 205 | 2257 | 0 | 205 | 0 | 1640 |

Figure 10:
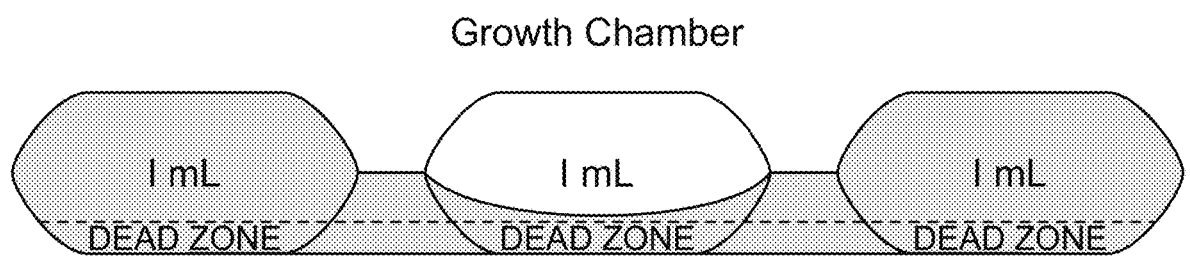
FIG. 10 is, according to some embodiments, a side-view cross sectional schematic illustration of an exemplary bioreactor, according to some embodiments.

If the volume in the mixer exceeds the designed maximum working volume of 2 mL, the mixing will be incomplete and there will be dead zones in the mixer as illustrated in FIG. 10. The dead zones will generally arise because the fluid will be stationary below the maximum deflection of the membrane. This can be a problem, especially for fed-batch cultures, since the volume of the micro-bioreactor is expected to exceed 2 mL throughout the entire culture after Day 0.

One way to address the volume variations within the bioreactor is to oversample for the fed-batch culture. An exemplary oversampling strategy is shown in the last column of Table 3. Table 3 includes the expected day to day working volumes (in microliters) of the RECA bioreactor for batch culture, fed-batch culture, and fed-batch culture with oversampling to prevent over-filling of the bioreactor. The fed-batch protocol is assumed to include a feed that leads to a 10% increase in volume in days 1, 3, 5, 7, and 9. If the bioreactor is oversampled to maintain a maximum volume of 2 mL, liquid can be added every day except Days 6-8 and Days 12-14. This is an additional advantage of the oversampling strategy. On days in which closed loop evaporation compensation cannot be performed, injections of fluid can be made by adding an amount of fluid that corresponds to the amount of fluid lost from the bioreactor via evaporation.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of operating a bioreactor, comprising:
performing for a period of time, within the bioreactor, a biochemical reaction in which at least one eukaryotic cell is grown within a liquid medium having a volume of less than about 50 milliliters, wherein the bioreactor consists of: a gas inlet conduit and a gas outlet conduit connected to the bioreactor, a gas bypass conduit that connects the gas inlet conduit and the gas outlet conduit, wherein the gas bypass conduit is external to the bioreactor, a $CO_2$ sensor configured to determine the $CO_2$ concentration within the bioreactor, and an optical density (OD) sensor configured to determine the eukaryotic cell density within the bioreactor;
adding a first amount of liquid to the liquid medium in the bioreactor during the period of time;
removing a second amount of liquid from the liquid medium in the bioreactor during the period of time; and
monitoring the volume of liquid within the bioreactor during the period of time;
wherein, during at least about 80% of the period of time, the total volume of liquid within the bioreactor does not fluctuate by more than about 20% from an average of the volume of liquid within the bioreactor; and wherein the bioreactor has a working volume of 2 milliliters or greater and less than about 50 milliliters.

2. A method of operating a bioreactor, comprising:
performing for a period of time, within the bioreactor, a biochemical reaction in which at least one eukaryotic cell is grown within a liquid medium having a volume of less than about 50 milliliters, wherein the bioreactor consists of: a gas inlet conduit and a gas outlet conduit connected to the bioreactor, a gas bypass conduit that connects the gas inlet conduit and the gas outlet conduit, wherein the gas bypass conduit is external to the bioreactor, a $CO_2$ sensor configured to determine the $CO_2$ concentration within the bioreactor, and an optical density (OD) sensor configured to determine the eukaryotic cell density within the bioreactor;
adding a first amount of liquid to the liquid medium in the bioreactor during the period of time;
removing a second amount of liquid from the liquid medium in the bioreactor during the period of time; and
monitoring the volume of liquid within the bioreactor during the period of time;
wherein, during at least about 80% of the period of time, the total volume of liquid within the bioreactor does not fluctuate by more than about 20% from an average of the volume of liquid within the bioreactor, and the osmolarity of the liquid medium within the bioreactor is maintained within a range of from about 200 osmoles per kilogram of the liquid medium to about 600 osmoles per kilogram of the liquid medium; and wherein the bioreactor has a working volume of 2 milliliters or greater and less than about 50 milliliters.

3. The method of claim 1, wherein, during at least about 90% of the period of time, the total volume of liquid within the bioreactor does not fluctuate by more than about 20% from an average of the volume of liquid within the bioreactor.

4. The method of claim 1, wherein, during at least about 80% of the period of time, the total volume of liquid within the bioreactor does not fluctuate by more than about 10% from an average of the volume of liquid within the bioreactor.

5. The method of claim 1, wherein the adding step is performed over a first period during the period of time, the removing step is performed over a second period during the period of time, and the first and second periods do not substantially overlap with each other.

6. A method of operating a bioreactor, comprising:
performing for a period of time, within a bioreactor, a biochemical reaction in which at least one eukaryotic cell is grown within a liquid medium having a volume of less than about 50 milliliters, wherein the bioreactor consists of: a gas inlet conduit and a gas outlet conduit connected to the bioreactor, a gas bypass conduit that connects the gas inlet conduit and the gas outlet conduit, wherein the gas bypass conduit is external to the bioreactor, a $CO_2$ sensor configured to determine the $CO_2$ concentration within the bioreactor, and an optical density (OD) sensor configured to determine the eukaryotic cell density within the bioreactor;
adding a first amount of liquid to the liquid medium in the bioreactor during a first period during the period of time;
removing a second amount of liquid having a volume that is within 10% of a volume of the first amount of liquid from the liquid medium in the bioreactor during a second period during the period of time, wherein the first period and the second period do not overlap;
repeating the adding and removing steps at least one time during the period of time; and
monitoring the volume of liquid within the bioreactor during the period of time;
wherein the adding step and the removing step are performed such that, between the adding step and the removing step, substantially no liquid is removed from the bioreactor via a non-evaporative pathway, and substantially no liquid is added to the bioreactor during the period of time; and wherein the bioreactor has a working volume of 2 milliliters or greater and less than about 50 milliliters.

7. A method of operating a bioreactor, comprising:
performing for a period of time, within the bioreactor, a biochemical reaction in which at least one eukaryotic cell is grown within a liquid medium having a volume of less than about 50 milliliters, wherein the bioreactor consists of: a gas inlet conduit and a gas outlet conduit connected to the bioreactor, a gas bypass conduit that connects the gas inlet conduit and the gas outlet conduit, wherein the gas bypass conduit is external to the bioreactor, a $CO_2$ sensor configured to determine the $CO_2$ concentration within the bioreactor, and an optical density (OD) sensor configured to determine the eukaryotic cell density within the bioreactor;
adding a first amount of liquid to the liquid medium in the bioreactor during a first period during the period of time;
removing a second amount of liquid having a volume that is within 10% of a volume of the first amount of liquid from the liquid medium in the bioreactor during a second period during the period of time, wherein the first period and the second period do not overlap;
repeating the adding and removing steps at least one time over the period of time; and
monitoring the volume of liquid within the bioreactor during the period of time;
wherein the adding step and the removing step are performed such that, between the adding step and the removing step, substantially no liquid is removed from the bioreactor via a non-evaporative pathway, and substantially no liquid is added to the bioreactor during the period of time, and
wherein, during at least about 80% of the period of time, the osmolarity of the liquid medium within the bioreactor is maintained within a range of from about 200 osmoles per kilogram of the liquid medium to about 600 osmoles per kilogram of the liquid medium; and wherein the bioreactor has a working volume of 2 milliliters or greater and less than about 50 milliliters.

8. The method of claim 6, wherein the adding step and the removing step are performed such that, between the adding step and the removing step, substantially no liquid is removed from the bioreactor.

9. The method of claim 6, wherein the second amount of liquid has a volume that is within 5% of the volume of the first amount of liquid.

10. The method of claim 9, wherein the second amount of liquid has a volume that is within 1% of the volume of the first amount of liquid.

11. The method of claim 1, wherein the biochemical reaction is performed within a liquid medium having a volume of less than about 10 milliliters.

12. The method of claim 11, wherein the biochemical reaction is performed within a liquid medium having a volume of less than about 5 milliliters.

13. The method of claim 1, wherein adding the first amount of liquid to the liquid medium comprises transporting the first amount of liquid into the bioreactor via a liquid inlet.

14. The method of claim 13, wherein the liquid inlet comprises a channel.

15. The method of claim 14, wherein the channel comprises a microfluidic channel.

16. The method of claim 1, wherein removing the second amount of liquid from the liquid medium in the bioreactor comprises transporting the second amount of liquid out of the bioreactor via a liquid outlet.

17. The method of claim 16, wherein the liquid outlet comprises a channel.

18. The method of claim 17, wherein the channel comprises a microfluidic channel.

19. The method of claim 1, wherein the liquid medium comprises a cell growth medium.

20. The method of claim 1, wherein the at least one eukaryotic cell is at least one mammalian cell.

21. The method of claim 20, wherein the at least one mammalian cell is a Chinese hamster ovary (CHO) cell.

22. The method of claim 2, wherein the at least one eukaryotic cell is at least one mammalian cell.

23. The method of claim 22, wherein the at least one mammalian cell is a Chinese hamster ovary (CHO) cell.

24. The method of claim 6, wherein the at least one eukaryotic cell is at least one mammalian cell.

25. The method of claim 24, wherein the at least one mammalian cell is a Chinese hamster ovary (CHO) cell.

26. The method of claim 7, wherein the at least one eukaryotic cell is at least one mammalian cell.

27. The method of claim 26, wherein the at least one mammalian cell is a Chinese hamster ovary (CHO) cell.

* * * * *

UNITED STATES PATENT AND TRADEMARK OFFICE
CERTIFICATE OF CORRECTION

| | | |
|---|---|---|
| PATENT NO. | : 11,827,871 B2 | Page 1 of 1 |
| APPLICATION NO. | : 16/673805 | |
| DATED | : November 28, 2023 | |
| INVENTOR(S) | : Goh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 177 days.

Signed and Sealed this
Twelfth Day of November, 2024

*Katherine Kelly Vidal*
Katherine Kelly Vidal
*Director of the United States Patent and Trademark Office*